(12) United States Patent
Cohen et al.

(10) Patent No.: US 7,890,185 B2
(45) Date of Patent: *__Feb. 15, 2011__

(54) TREATMENT OF DISORDERS BY UNIDIRECTIONAL NERVE STIMULATION

(75) Inventors: Ehud Cohen, Ganei Tikva (IL); Yossi Gross, Moshav Mazor (IL); Shai Ayal, Jerusalem (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 1361 days.

This patent is subject to a terminal disclaimer.

(21) Appl. No.: 10/722,589

(22) Filed: Nov. 25, 2003

(65) Prior Publication Data

US 2004/0172094 A1    Sep. 2, 2004

Related U.S. Application Data

(63) Continuation of application No. 09/944,913, filed on Aug. 31, 2001, now Pat. No. 6,684,105.

(51) Int. Cl.
*A61N 1/00*    (2006.01)
(52) U.S. Cl. .................. 607/118; 607/40; 607/45; 607/46; 607/62
(58) Field of Classification Search .............. 607/63, 607/40, 45–46, 62, 148–149, 118
See application file for complete search history.

(56) References Cited

U.S. PATENT DOCUMENTS

| | | |
|---|---|---|
| 3,411,507 A | 11/1968 | Wingrove |
| 4,161,952 A | 7/1979 | Kinney et al. |
| 4,535,785 A | 8/1985 | van den Honert |
| 4,573,481 A | 3/1986 | Bullara |
| 4,602,624 A | 7/1986 | Naples |
| 4,608,985 A | 9/1986 | Crish |
| 4,628,942 A | 12/1986 | Sweeney |
| 4,649,936 A | 3/1987 | Ungar |
| 4,702,254 A | 10/1987 | Zabara |
| 4,739,764 A | 4/1988 | Lue |

(Continued)

FOREIGN PATENT DOCUMENTS

EP    0831954    4/1998

(Continued)

OTHER PUBLICATIONS

U.S. Appl. No. 60/263,834, entitled "Selective Blocking of Nerve Fibers", filed Jan. 25, 2001.

(Continued)

*Primary Examiner*—Mark W Bockelman
(74) *Attorney, Agent, or Firm*—John P. White; Cooper & Dunham LLP

(57) ABSTRACT

Apparatus for treating a condition of a subject is provided. An electrode device is adapted to be coupled to longitudinal nervous tissue of the subject, and a control unit is adapted to drive the electrode device to apply to the nervous tissue a current which is capable of inducing action potentials that propagate in the nervous tissue in a first direction, so as to treat the condition. The control unit is further adapted to suppress action potentials from propagating in the nervous tissue in a second direction opposite to the first direction.

74 Claims, 7 Drawing Sheets

U.S. PATENT DOCUMENTS

| | | |
|---|---|---|
| 4,867,164 A | 9/1989 | Zabara |
| 4,962,751 A | 10/1990 | Krauter |
| 5,025,807 A | 6/1991 | Zabara |
| 5,042,497 A | 8/1991 | Shapland |
| 5,058,599 A | 10/1991 | Andersen et al. |
| 5,170,802 A | 12/1992 | Mehra |
| 5,188,104 A | 2/1993 | Wernicke |
| 5,199,430 A | 4/1993 | Fang |
| 5,205,285 A | 4/1993 | Baker, Jr. |
| 5,215,086 A | 6/1993 | Terry, Jr. |
| 5,224,491 A | 7/1993 | Mehra |
| 5,263,480 A | 11/1993 | Wernicke |
| 5,282,468 A | 2/1994 | Klepinski |
| 5,292,344 A | 3/1994 | Douglas |
| 5,299,569 A | 4/1994 | Wernicke |
| 5,335,657 A | 8/1994 | Terry, Jr. |
| 5,411,531 A | 5/1995 | Hill et al. |
| 5,423,872 A | 6/1995 | Cigaina |
| 5,437,285 A | 8/1995 | Verrier et al. |
| 5,507,784 A | 4/1996 | Hill et al. |
| 5,540,730 A | 7/1996 | Terry, Jr. |
| 5,540,734 A | 7/1996 | Zabara |
| 5,571,150 A | 11/1996 | Wernicke |
| 5,578,061 A | 11/1996 | Stroetmann et al. |
| 5,615,684 A | 4/1997 | Hagel et al. |
| 5,645,570 A | 7/1997 | Corbucci et al. |
| 5,690,691 A | 11/1997 | Chen |
| 5,707,400 A | 1/1998 | Terry, Jr. |
| 5,716,385 A | 2/1998 | Mittal |
| 5,755,750 A | 5/1998 | Petruska |
| 5,836,994 A | 11/1998 | Bourgeois |
| 6,026,326 A | 2/2000 | Bardy |
| 6,058,328 A | 5/2000 | Levine et al. |
| 6,073,048 A | 6/2000 | Kieval et al. |
| 6,083,249 A | 7/2000 | Familoni |
| 6,091,922 A | 7/2000 | Bisaiji |
| 6,097,984 A | 8/2000 | Douglas |
| 6,104,955 A | 8/2000 | Bourgeois |
| 6,104,956 A | 8/2000 | Naritoku et al. |
| 6,161,029 A | 12/2000 | Spreigl et al. |
| 6,167,304 A | 12/2000 | Loos |
| 6,205,359 B1 | 3/2001 | Boveja |
| 6,240,314 B1 | 5/2001 | Plicchi et al. |
| 6,272,377 B1 | 8/2001 | Sweeney et al. |
| 6,319,241 B1 | 11/2001 | King |
| 6,341,236 B1 | 1/2002 | Osorio |
| 6,381,499 B1 | 4/2002 | Taylor et al. |
| 6,400,982 B2 | 6/2002 | Sweeney et al. |
| 6,493,585 B2 | 12/2002 | Plicchi et al. |
| 6,522,926 B1 | 2/2003 | Kieval et al. |
| 6,542,774 B2 | 4/2003 | Hill et al. |
| 6,564,096 B2 | 5/2003 | Mest |
| 6,571,122 B2 | 5/2003 | Schroeppel et al. |
| 6,587,727 B2 | 7/2003 | Osorio et al. |
| 6,600,954 B2 | 7/2003 | Cohen et al. |
| 6,610,713 B2 | 8/2003 | Tracey |
| 6,622,041 B2 | 9/2003 | Terry, Jr. et al. |
| 6,628,987 B1 | 9/2003 | Hill et al. |
| 6,671,556 B2 | 12/2003 | Osorio et al. |
| 6,684,105 B2 | 1/2004 | Cohen et al. |
| 6,690,971 B2 | 2/2004 | Schauerte et al. |
| RE38,705 E | 2/2005 | Hill et al. |
| 6,865,416 B2 | 3/2005 | Dev et al. |
| 6,885,888 B2 | 4/2005 | Rezai |
| 6,907,293 B2 | 6/2005 | Grill et al. |
| 6,985,774 B2 | 1/2006 | Kieval et al. |
| 7,050,846 B2 | 5/2006 | Sweeney et al. |
| 7,076,299 B2 | 7/2006 | Thong |
| 7,076,307 B2 | 7/2006 | Boveja et al. |
| 7,123,961 B1 | 10/2006 | Kroll et al. |
| 2002/0035335 A1 | 3/2002 | Schauerte |
| 2002/0107553 A1 | 8/2002 | Hill et al. |
| 2003/0195574 A1 | 10/2003 | Osorio et al. |
| 2003/0216775 A1 | 11/2003 | Hill et al. |
| 2003/0233129 A1 | 12/2003 | Matos |
| 2004/0048795 A1 | 3/2004 | Ivanova et al. |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0215289 A1 | 10/2004 | Fukui |
| 2004/0249416 A1 | 12/2004 | Yun et al. |
| 2005/0131467 A1 | 6/2005 | Boveja |
| 2005/0222644 A1 | 10/2005 | Killian et al. |
| 2006/0047325 A1 | 3/2006 | Thimineur et al. |
| 2006/0052831 A1 | 3/2006 | Fukui |
| 2006/0064140 A1 | 3/2006 | Whitehurst et al. |
| 2006/0129205 A1 | 6/2006 | Boveja et al. |
| 2006/0149337 A1 | 7/2006 | John |
| 2006/0167498 A1 | 7/2006 | DiLorenzo |

FOREIGN PATENT DOCUMENTS

| | | |
|---|---|---|
| WO | WO-01/10375 A2 | 2/2001 |
| WO | WO-2006/102370 A2 | 9/2006 |

OTHER PUBLICATIONS

Ungar, I. J., et al. "Generation of Unidirectionally Propagating Action Potentials Using a Monopolar Electrode Cuff", Annals of Biomedical Engineering, vol. 14, pp. 437-450, 1986.

Sweeney, James D., et al. "An Asymmetric Two Electrode Cuff for Generation of Unidirectionally Propagated Action Potentials", IEEE Transactions on Biomedical Engineering, vol. BME-33, No. 6, Jun. 1986.

Naples, Gregory G., et al. "A Spiral Nerve Cuff Electrode for Peripheral Nerve Stimulation", IEEE Transactions of Biomedical Engineering, vol. 35, No. 11, Nov. 1998, pp. 905-916.

Sweeney, James D., et al. "A Nerve Cuff Technique for Selective Excitation of Peripheral Nerve Trunk Regions", IEEE Transactions on Biomedical Engineering, vol. 37, No. 7, Jul. 1990.

Van Den Honert, et al. "Generation of Unidirectionally Propagated Action Potentials in a Peripheral Nerve by Brief Stimuli", Science magazine, vol. 206, Dec. 14, 1979, pp. 1311-1312.

Van Den Honert, et al. "A Technique for Collision Block of Peripheral Nerve: Frequency Dependence", IEEE Transactions of Biomedical Engineering, vol. BME-28, No. 5, May 1981, pp. 379-382.

Rijkhoff, N.J.M., et al. "Orderly recruitment of motoneurons in an acute rabbit model", 20th Annual International Conference of the IEEE Engineering in Medicine and Biology Society, vol. 20, No. 5, 1998, pp. 2564-2565.

Baratta, et al. "Orderly stimulation of Skeletal Muscle Motor Units with Tripolar Nerve Cuff Electrode", IEEE Transactions of Biomedical Engineering, vol. 36, No. 8, Aug. 1989, pp. 836-843.

Devor, M. "Pain Networks", Handbook of Brand Theory and Neural Networks, Ed. M.A. Arbib, MIT Press, p. 698, 1998.

U.S. Appl. No. 09/824,682 entitled "Method and Apparatus for Selective Control of Nerve Fibers" filed Apr. 4, 2001.

Cortese, J.F. "Vagus Nerve Stimulation for Control of Intractable Epileptic Seizures" available at http://www.science.wayne.edu/~bio340/StudentPages/corese/, May 31, 2001.

Website: http://www.bcm.tmc.edu/neurol/struct/epilep/epilipsy_vagus.html, May 31, 2001.

Fitzpatrick, et al. "A Nerve Cuff Design for the Selective Activation and Blocking of Myelinated Nerve Fibres", Annual Conference of the IEEE Engineering in Medicine and Biology Society, vol. 13, No. 2, 1991.

Carlson MD et al., "Selective stimulation of parasympathetic nerve fibers to the human sinoatrial node," Circuation 85:1311-1317 (1992).

Page PL et al., "Regional distribution of atrial electrical changes induced by stimulation of extracardiac and intracardiac neural elements," J Thorac Cardiovasc Surg. 109(2):377-88 (1995).

Furukawa Y et al., "Differential blocking effects of atropine and gallamine on negative chrontropic and dromotropic responses to vagus stimulation in anesthetized dogs," J Pharmacol Exp. Ther. 251(3):797-802 (1989).

Bluemel KM, "Parasympathetic postganglionic pathways to the sinoatrial node," J Physiol. 259 (5 Pt 2): H1504-10 (1990).

Mazgalev TN, "AV Nodal Physiology," Heart Rhythm Society (www.hrsonline.org), no date.

Bibevski S et al. "Ganglionic Mechanisms Contribute to Diminished Vagal Control in Heart Failure," Circulation 99:2958-2963 (1999).

Garrigue S et al., "Post-ganglionic vagal stimulation of the atrioventricular node reduces ventricular rate during atrial fibrillation,"Pace 21(4), Part II, 878 (1998).

Chen SA et al., "Intracardiac stimulation of human parasympathetic nerve fibers induces negative dromotropic effects: implication with the lesions of radiofrequency catheter ablation," J Cardiovasc Electrophysiol. 9(3):245-52 (1998).

Cooper et al., "Neural effects on sinus rate and atrial ventricular conduction produced by electrical stimulation from a transvenous electrode catheter in the canine right pulmonary artery" Circ Res vol. 46(1):48-57 (1980).

Waninger MS et al., "Electrophysiological control of ventricular rate during atrial fibrillation," PACE 23:1239-1244 (2000).

Goldberger JJ et al., "New technigue for vagal nerve stimulation," J Neurosci Methods. 91(1-2):1089-14 (1999).

Fang, et al., 1991. "Selective activation of small motor axons by quasitrapezoidal current pulses". IEEE Transactions on Biomedical Engineering 38: 168-174.

Stampfli, Robert, 1954. "Saltatory conduction in nerve". Physiol. Rev. 34: 101-112.

Schaldach M, "New concepts in electrotherapy of the heart", Electrotherapy of the Heart, Springer Verlag Heidelberg, pp. 210-214 (1992).

Advisory Action issued Mar. 4, 2003 during the prosecution of U.S. Appl. No. 09/824,682.

Office Action issued Jul. 17, 2002 during the prosecution of U.S. Appl. No. 09/824,682.

Office Action issued Jun. 27, 2008 during the prosecution of U.S. Appl. No. 10/205,475.

Final Office Action issued Jan. 23, 2003 during the prosecution of U.S. Appl. No. 09/824,682.

Manfredi, M., (1970) "Differential Block of Conduction of Larger Fibers in Peripheral Nerve by Direct Current," *Archives italiennes de biologie*, 108(1): 52-71.

Rattay, F., (1989) "Analysis of models for extracellular fiber stimulation," *IEEE Transactions on Biomedical Engineering*, 36(2): 676-682.

Rijkhoff, N.J. et al., (1998) "Orderly recruitment of motoneurons in an acute rabbit model," *Proc. of the Annual Conf. of the IEEE Engineering in Medicine and Biology Society*, 20(5): 2564-2565.

Nov. 1, 2007 Office Action issued by the U.S. Patent and Trademark office in connection with U.S. Appl. No. 10/205,475.

Jones, J. F. X. et al., (1995) "Heart Rate Responses to Selective Stimulation of Cardiac Vagal C Fibres in Anaesthetized Cats, Rats and Rabbits," *Journal of Physiology*, 489(1): 203-214.

Jones, J.F.X. et al., (1998) "Activity of C Fibre Cardiac Vagal Efferents in Anaesthetized Cats and Rats," Journal of Physiology, 507(3) 869-880.

Apr. 5, 2007 Office Action, issued by the U.S. Patent and Trademark Office, in connection with U.S. Appl. No. 10/488,334.

Apr. 25, 2008 Office Action, issued by the U.S. Patent and Trademark Office, in connection with U.S. Appl. No. 10/488,334.

Van den Hoert et al., (1979) "Generation of unidirectionally propogated action potentials in a peripheral nerve brief stimuli", Science, vol. 206: 1311-1312.

TREATMENT OF DISORDERS BY UNIDIRECTIONAL NERVE STIMULATION

CROSS-REFERENCES TO RELATED APPLICATIONS

This application is a continuation of U.S. patent application 09/944,913, filed Aug. 31, 2001, now U.S. Pat. No. 6,684,105 entitled, "Treatment of disorders by unidirectional nerve stimulation," which issued as U.S. Pat. No. 6,684,105.

FIELD OF THE INVENTION

The present invention relates generally to treating patients by application of electrical signals to a selected nerve or nerve bundle, and specifically to methods and apparatus for stimulating nerve tissue while minimizing possible accompanying side effects.

BACKGROUND OF THE INVENTION

The use of nerve stimulation for treating and controlling a variety of medical, psychiatric, and neurological disorders has seen significant growth over the last several decades. In particular, stimulation of the vagus nerve (the tenth cranial nerve) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion). The vagus nerve is responsible for controlling and/or receiving feedback from various glands, the pharynx, larynx, heart, lungs, liver, stomach, intestine, and ureters. Because of its large number of functions with respect to a range of body systems, the vagus nerve is preferred in many applications for purposes of modulating the functions of designated organs or portions of the central nervous system (CNS).

U.S. Pat. No. 5,540,730 to Terry et al., which is incorporated herein by reference, describes a method for treating motility disorders by applying a signal to the vagus nerve of a patient, in inhibit neural impulses, and produce excitatory or inhibitory neurotransmitter release by the nerve, according to the specific nature of the motility disorder.

U.S. Pat. Nos. 5,188,104 and 5,263,480 to Wernicke et al., which are incorporated herein by reference, describe a method for treating compulsive eating disorders by applying a stimulating signal to the vagus nerve of the patient appropriate to alleviate the effect of the eating disorder. For example, in cases where the disorder is compulsive eating, the stimulating signal is described as being calibrated to produce a sensation of satiety in the patient. In cases where the disorder is compulsive refusal to eat (anorexia nervosa), the stimulating signal is described as being calibrated to produce a sensation of hunger or to suppress satiety in the patient.

U.S. Pat. No. 5,571,150 to Wernicke et al., which is incorporated herein by reference, describes a method for treating a comatose patient by stimulating a cranial nerve, preferably the vagus nerve, in order to modulate the activity of the nerve in an effort to rouse the patient from the coma.

U.S. Pat. Nos. 4,702,254, 4,867,164 and 5,025,807 to Zabara, which are incorporated herein by reference, generally describe methods for controlling or preventing epileptic seizures and other motor disorders by stimulating the vagus nerve.

U.S. Pat. No. 6,205,359 to Boveja, which is incorporated herein by reference, describes apparatus for treating various forms of epilepsy and involuntary movement disorders by electrical stimulation of the left vagus nerve.

U.S. Pat. No. 5,205,285 to Baker, which is incorporated herein by reference, describes a device designed to avoid undesirable voice modulation of patients undergoing vagal stimulation therapy, while maintaining a bias in certain circumstances toward ongoing delivery of the therapy. In essence, this device requires the addition of sensing means to detect the patient's attempts at speech, responsive to which the device halts or delays the vagal stimulation during the time that speech attempts continue to be detected.

U.S. Pat. No. 5,299,569 to Wernicke et al., which is incorporated herein by reference, describes a method for treating and controlling neuropsychiatric disorders, including schizophrenia, depression and borderline personality disorder, by selectively applying a predetermined electrical signal to the patient's vagus nerve, in order to alleviate the symptoms of the disorder being treated.

U.S. Pat. No. 5,335,657 to Terry et al., which is incorporated herein by reference, describes a method for treating and controlling sleep disorders by applying an electrical signal to the vagus nerve in order to modulate electrical activity of afferent fibers of the nerve.

U.S. Pat. No. 5,707,400 to Terry et al., which is incorporated herein by reference, describes a method for treating patients suffering from refractory hypertension, also by stimulating the vagus nerve.

As is seen from this list of patents, stimulation of the nervous system, particularly the vagus nerve, for therapeutic purposes has been the subject of a considerable amount of research and application to medical, psychiatric, and neurological disorders. However, other than the problem of speech impairment addressed by the above-cited U.S. Pat. No. 5,205, 285 to Baker, the possible unwanted side effects, both proven and potential, of selective stimulation of the vagus nerve, have not been given extensive consideration.

U.S. Pat. No. 5,282,468 to Klepinski, which is incorporated herein by reference, describes an implantable neural electrode.

U.S. Pat. No. 4,628,942 to Sweeney et al., which is incorporated herein by reference, describes an asymmetric, shielded, two-electrode cuff for stimulating a nerve.

U.S. Pat. No. 4,535,785 to van den Honert et al., describes implantable electronic apparatus.

U.S. Pat. No. 4,602,624 to Naples et al., which is incorporated herein by reference, describes an implantable electrode cuff for applying signals to nerves.

U.S. Pat. No. 5,199,430 to Fang et al., which is incorporated herein by reference, describes implantable electronic apparatus for assisting the urinary sphincter to relax.

U.S. Pat. No. 5,215,086 to Terry et al., which is incorporated herein by reference, describes a method for applying electrical stimulation to treat migraine headaches.

U.S. Pat. No. 5,755,750 to Petruska et al., which is incorporated herein by reference, describes a method for selectively inhibiting activity in nerve fibers.

U.S. Pat. No. 4,649,936 to Ungar et al., and U.S. Pat. No. 4,608,985 to Chrish et al., which are incorporated herein by reference, describe apparatus and methods for selectively blocking action potentials passing along a nerve trunk. PCT Patent Publication WO 01/10375A2 to Felsen et al., which is incorporated herein by reference, describes a method for inhibiting action potential generation in nervous tissue.

The following articles may be of interest, and are incorporated herein by reference:

"Generation of unidirectionally propagating action potentials using a monopolar electrode cuff," Annals of Biomedical Engineering, vol. 14, pp. 437-450, 1986 by Ira J. Ungar et al.

"An asymmetric two electrode cuff for generation of unidirectionally propagated action potentials," IEEE Transactions on Biomedical Engineering, vol. BME-33, No. 6, June 1986 by James D. Sweeney et al.

"A spiral nerve cuff electrode for peripheral nerve stimulation," by Gregory G. Naples et al., IEEE Transactions on Biomedical Engineering, vol. 35, No. 11, November 1988.

"A nerve cuff technique for selective excitation of peripheral nerve trunk regions," by James D. Sweeney et al., IEEE Transactions on Biomedical Engineering, vol. 37, No. 7, July 1990.

"Generation of unidirectionally propagated action potentials in a peripheral nerve by brief stimuli," Science, vol. 206, pp. 1311-1312, December 1979.

"Generation of unidirectionally propagated action potentials in a peripheral nerve by brief stimuli," van den Honert et al., 206 Science 1311-1312, (Dec. 14, 1979).

"A technique for collision block of peripheral nerve: Frequency dependence," van den Honert, C., Mortimer, J. T.: MP-12, IEEE Trans. Biomed. Eng. 28:379-382, 1981.

"A technique for collision block of peripheral nerve: Single stimulus analysis," van den Honert, C., Mortimer, J. T.: MP-11, IEEE Trans. Biomed. Eng. 28:373-378, 1981.

"A Nerve Cuff Design for the Selective Activation and Blocking of Myelinated Nerve Fibers," D.M. Fitzpatrick et al., Ann. Conf. of the IEEE Eng. in Medicine and Biology Soc., Vol. 13, No. 2, pp. 906, 1991. The authors describe the use of a tripolar cuff electrode for generating unidirectional action potentials in nerve fibers according to their size, and conclude, "The results show that a tripolar cuff electrode can generate unidirectional action potentials in the small nerve fibres whilst blocking the large fibres. Changing the ratio of the anodal currents results in the gradual recruitment of the large fibres" (p. 907).

"Acute Animal Studies on the Use of Anodal Block to Reduce Urethral Resistance in Sacral Root Stimulation," N.J.M. Rijkhof et al., IEEE Transactions on Rehabilitation Engineering, Vol. 2, No. 2, pp. 92, 1994. The authors describe experiments in which, using a tripolar electrode configuration and monophasic rectangular current pulses in acute canine experiments, a reduction of intraurethral pressure response, as compared to stimulation without blocking, of more than 80% was achieved. The authors write, "Our research is focused on selective activation of small nerve fibers in sacral roots by a combination of cathodal excitation of all fibers and a selective anodal block [1], [6]-[8] of the large fibers. . . . Since large diameter fibers need less current for their blocking than small ones [1], selective activation of small fibers is possible by blocking, distal to the excitation site (cathode), the propagation of the induced action potentials in the large fibers" (p. 92).

"Orderly Recruitment of Motoneurons in an Acute Rabbit Model," N.J.M. Rijkhoff et al., Ann. Conf. of the IEEE Eng., Medicine and Biology Soc., Vol. 20, No. 5, pp. 2564, 1998. The authors describe the use of selective anodal blocking in an acute animal model to investigate the advantages of orderly recruitment. The authors write, "At least 3 different methods are known that allow for selective small fiber activation, selective anodal blocking, high frequency stimulation and slowly rising pulses [2]. A project has been started to compare these 3 different methods with respect to performance, stability, required electrical charge per pulse. This abstract reports on the results obtained with only one of these methods, the selective anodal block [3]" (p. 2564).

"Orderly Stimulation of Skeletal Muscle Motor Units with Tripolar Nerve Cuff Electrode," R. Bratta et al., IEEE Transactions on Biomedical Engineering, Vol. 36, No. 8, pp. 836, 1989. The authors describe an electrical nerve stimulation technique, using a single tripolar electrode, that is capable of recruiting motor units according to their size, while allowing simultaneous but independent control of firing rate in the active units.

U.S. Pat. No. 5,423,872 to Cigaina, which is incorporated herein by reference, describes a method for pacing the stomach in order to alter its natural rhythm. The principle espoused in Cigaina is that by altering the rhythm, one can either delay or speed up gastric emptying. Cigaina indicates that many different disorders, including gastroesophageal reflux disorder (GERD), can be treated using the rhythm altering method.

U.S. Pat. No. 5,716,385 to Mittal et al., which is incorporated herein by reference, describes a system to treat GERD by stimulating the skeletal muscle tissue of the crural diaphragm whenever myoelectric measurements made on the diaphragm are indicative of relaxation thereof. Stimulation of the diaphragm is intended to indirectly cause contraction of the lower esophageal sphincter (LES), and thereby inhibit a reflux event which is assumed to accompany relaxation of the diaphragm.

U.S. Pat. No. 6,097,984 to Douglas, which is incorporated herein by reference, discloses a system to treat GERD by continually simulating the LES of a patient in order to maintain it in a closed state, thereby preventing reflux. Stimulation is removed only when swallowing is detected, to allow food pass into the stomach.

U.S. Pat. Nos. 6,104,955, 6,091,992, and 5,836,994 to Bourgeois, U.S. Pat. No. 6,026,326 to Bardy, U.S. Pat. No. 6,083,249 to Familoni, U.S. Pat. No. 5,690,691 to Chen, U.S. Pat. No. 5,292,344 to Douglas, and U.S. Pat. No. 3,411,507 to Wingrove, which are incorporated herein by reference, describe methods and apparatus for electrical simulation of the GI tract to treat various physiological disorders.

SUMMARY OF THE INVENTION

It is an object of some aspects of the present invention to provide apparatus and methods for treating and controlling a medical condition by application of electrical signals to a selected nerve or nerve bundle.

It is also an object of some aspects of the present invention to provide apparatus and methods for treating and controlling a medical condition by application of electrical signals to a selected nerve or nerve bundle while minimizing adverse side effects.

It is a further object of some aspects of the present invention to provide apparatus and methods for treatment of sleep disorders while minimizing adverse side effects.

It is still a further object of some aspects of the present invention to provide apparatus and methods for treatment of neuropsychiatric disorders while minimizing adverse side effects.

It is yet a further object of some aspects of the present invention to provide apparatus and methods for treatment of eating disorders, while minimizing adverse side effects caused by stimulation of the nerves controlling the digestive system.

It is an additional object of some aspects of the present invention to provide apparatus and methods for treatment of motility disorders, while minimizing undesired side effects caused by stimulation of the nerves controlling the digestive system.

It is yet an additional object of some aspects of the present invention to provide apparatus and methods for rousing comatose patients, while minimizing adverse effects upon physiological functions.

It is still an additional object of some aspects of the present invention to provide apparatus and methods for treating epilepsy and involuntary movement disorders while minimizing unwanted side effects such as impairment of speech.

It is also an object of some aspects of the present invention to provide apparatus and methods for treating hypertension while minimizing unwanted side effects.

In preferred embodiments of the present invention, apparatus for treating a specific condition comprises a set of one or more electrode devices that are applied to one or more selected sites of the central or peripheral nervous system of a patient. A control unit preferably drives the electrode devices to: (a) apply signals which induce the propagation of nerve impulses in a desired direction in order to treat the condition, and (b) suppress artificially-induced nerve impulses in the opposite direction in order to minimize adverse side effects of the signal application.

For some applications of the present invention, the signal is applied to a nerve such as the vagus nerve, in order to stimulate efferent fibers and increase the motor activity of the small intestine and colon, and thereby treat motility disorders. Simultaneously, action potential propagation is inhibited in afferent fibers responsive to the application of the signals. In the prior art, such as that described in the above-cited U.S. Pat. No. 5,540,730 to Terry et al., the vagus nerve is stimulated so as to influence the motor activity of the small intestine and colon. However, an unintended result of applying the method of the Terry patent is that, when the nerve is stimulated, action potentials are induced in both directions (stimulating afferent and efferent fibers). Stimulation of the vagus nerve as a whole may thus produce undesired afferent stimulation, which may in turn result in, for example, the initiation of undesired or counterproductive feedback to the brain, and resultant undesired sensations or activity of the digestive system (e.g., nausea). Advantageously, and unlike the prior art, application of these embodiments of the present invention substantially stimulates only the intended efferent fibers, and reduces or eliminates the transmission of sensory signals to the CNS that could cause such undesirable responses in the digestive system.

For some applications of the present invention, the signal is applied to a portion of the vagus nerve innervating the stomach in order to stimulate sensory fibers and thereby produce a sensation, e.g., satiety or hunger. In the prior art, such as that described in the above-cited U.S. Pat. No. 5,263,480 to Wernicke et al., the vagus nerve is stimulated so as to induce certain sensory messages to propagate to the brain. However, upon the application of stimulation as described by Wernicke, action potentials are induced in both directions—on afferent and efferent fibers—and may thus generate unwanted effector responses. Depending upon the location on the vagus nerve at which stimulation is applied, such impulses may, for example, stimulate the glands of the stomach to secrete excessive hydrochloric acid, or they may reduce or otherwise affect the heartbeat of the patient. Unlike the prior art, application of this embodiment of the present invention generates substantially only sensory signals, and generally does not cause efferent signals to be transmitted to the effectors that could result in such undesirable responses.

For some applications, the signal is applied to the vagus nerve so as to modulate electrical activity in the brain, and thereby rouse a patient from a comatose condition. At the same time, the electrode devices are driven to inhibit action potentials in efferent fibers which would generally arise as a result of the application of the signal. In the prior art, such as that described in U.S. Pat. No. 5,571,1.50 to Wernicke et al., the vagus nerve in the neck is stimulated so as to cause afferent nerve fibers to conduct modified electrical patterns toward the reticular formation. However, inadvertent stimulation of efferent fibers resulting from the bi-directional nature of artificial nerve stimulation may result in undesirable motor, glandular or cardiac activity. Unlike the prior art, this application of the present invention inhibits action potentials in the efferent fibers, and consequently generally does not cause unwanted efferents to be generated.

Alternatively, the signal is applied to the vagus nerve to treat epilepsy and involuntary movement disorders, while action potential propagation responsive to the signal in efferent fibers is suppressed. In the prior art, either the left or right vagus nerve is stimulated as described in the above-cited Zabara and Boveja patents. The basic premise of vagal nerve stimulation for control of epileptic seizures is that vagal afferents have a diffuse central nervous system (CNS) projection, and activation of these pathways has a widespread effect on neuronal excitability. However, the mechanism by which vagal stimulation exerts its influence on seizures is not well understood.

The inventors of the present invention believe that the techniques described in the Zabara and Boveja patents induce unintended and, at least to some extent, undesirable accompanying effects resulting from the stimulation of efferent fibers at the same time as the treatment is being applied. It is well known, for example, that stimulation of the right vagus can lead to profound bradycardia (slowing of the heartbeat), which is an unwanted and unnecessary complication. Additionally, it has been determined that a side effect of vagal stimulation in epileptic patients is the presence of a noticeable modulation or reduction of the patient's voice when he or she tries to speak during application of the stimulating signals to the nerve. U.S. Pat. No. 5,205,285 to Baker, cited above, addresses the problem of voice modulation, but requires the addition of a sensor to detect the patient's speech and simply terminates the vagal stimulation, i.e., the desired treatment, whenever speech attempts continue to be detected. A drawback of this solution is that beneficial therapy may be unduly inhibited in favor of cosmetic or secondary considerations. Unlike the limitations of the prior art, however, application of this embodiment of the present invention substantially precludes the onset of these accompanying effects by permitting nerve impulses to travel only in the desired direction.

For some applications of the present invention, the signal is applied to the vagus nerve in order to treat and control sleep disorders or hypertension, while inhibiting action potential propagation in efferent fibers responsive to the applied signal. In the prior art, such as that described in U.S. Pat. Nos. 5,335,657 and 5,707,400 to Terry et al., bi-directional impulses are generated by the stimulation, resulting in both the desired treatment as well as unintended and not necessarily beneficial accompanying physiological responses. Unlike the prior art, however, application of this embodiment of the present invention substantially does not stimulate electrical activity of efferent fibers that may generate unwanted visceral, glandular, or motor responses.

In summary, the stimulation of nerve impulses in one direction while suppressing impulses in the opposite direction is preferably used to obtain the benefits of various new or prior art therapeutic treatments, including, but not limited to, those described in the references cited herein, while reducing or eliminating adverse and/or unintended side effects.

There is therefore provided, in accordance with a preferred embodiment of the present invention, a method for treating a condition of a subject, including:

driving into longitudinal nervous tissue of the subject a current which is capable of inducing action potentials that propagate in the nervous tissue in a first direction, so as to treat the condition; and suppressing action potentials from propagating in the nervous tissue in a second direction opposite to the first direction.

Preferably, driving the current includes driving a current capable of inducing action potentials that propagate in the nervous tissue in an afferent direction with respect to the central nervous system of the subject. Alternatively, driving the current includes driving a current capable of inducing action potentials that propagate in the nervous tissue in an efferent direction with respect to the central nervous system of the subject.

Driving the current typically, but not necessarily, includes driving the current into a vagus nerve of the subject.

In a preferred embodiment, the method includes driving the current and suppressing the action potentials at substantially the same time.

For some applications, driving the current includes configuring the current to be capable of treating an involuntary movement disorder of the subject.

In a preferred embodiment, suppressing the action potentials includes regulating the suppressing of the action potentials so as to inhibit an undesired response of the central nervous system of the subject generated responsive to driving the current into the nervous tissue. For example, suppressing the action potentials may include regulating the suppressing of the action potentials so as to inhibit an undesired sensation generated responsive to driving the current into the nervous tissue.

Suppressing the action potentials typically includes suppressing action potentials induced responsive to driving the current.

As appropriate, driving the current may include configuring the current to be capable of treating one or more of the following exemplary conditions of the subject: a sleep disorder, a gastrointestinal motility disorder, an eating disorder, obesity, anorexia, a gastrointestinal tract disorder, hypertension, coma, or epilepsy. During epilepsy treatment, suppressing the action potentials typically includes suppressing action potentials that interfere with an ability of the subject to speak.

In a preferred embodiment, driving the current includes applying to a vagus nerve of the subject a current capable of inducing constriction of a lower esophageal sphincter of the subject.

Typically, suppressing the action potentials includes suppressing the action potentials repeatedly, during a series of temporally non-contiguous "action potential suppression periods." The method in this case preferably includes substantially withholding the suppressing of action potentials between the action potential suppression periods.

As appropriate, driving the current may include driving the current into nervous tissue of the central nervous system of the subject and/or into nervous tissue of the peripheral nervous system of the subject.

For some applications, suppressing the action potentials includes identifying an action potential conduction velocity and suppressing action potentials characterized by the identified conduction velocity. In this case, the method preferably includes withholding suppression of an action potential having a conduction velocity substantially different from the identified conduction velocity.

In some preferred embodiments of the present invention, suppressing the action potentials includes regulating the suppressing of the action potentials so as to inhibit an undesired effector action responsive to driving the current into the nervous tissue. For example, suppressing the action potentials may include suppressing generation of action potentials that induce: (a) increased acid secretion in a gastrointestinal tract of the subject, (b) muscular contraction, and/or (c) bradycardia.

Preferably, suppressing the action potentials includes applying an electric field to the nervous tissue. Further preferably, applying the field includes applying a plurality of electric fields to the nervous tissue at respective longitudinal sites thereof. Applying the plurality of electric fields to the nervous tissue typically includes applying each of the fields at a different respective time. Moreover, applying the fields at the respective longitudinal sites typically includes applying the fields at two adjacent sites separated by at least about 2 mm. Alternatively or additionally, applying the fields at the respective longitudinal sites includes applying the fields at two adjacent sites separated by less than about 4 mm.

In a preferred embodiment, the method includes sensing an indication of a presence of the condition, and driving the current includes driving the current responsive to sensing the indication. Alternatively or additionally, the method includes receiving an input from the subject, and driving the current includes driving the current responsive to receiving the input.

There is also provided, in accordance with a preferred embodiment of the present invention, apparatus for treating a condition of a subject, including:

an electrode device, adapted to be coupled to longitudinal nervous tissue of the subject; and a control unit, adapted to drive the electrode device to apply to the nervous tissue a current which is capable of inducing action potentials that propagate in the nervous tissue in a first direction, so as to treat the condition, and adapted to suppress action potentials from propagating in the nervous tissue in a second direction opposite to the first direction.

The present invention will be more fully understood from the following detailed description of the preferred embodiment thereof, taken together with the drawings, in which:

DETAILED DESCRIPTION OF PREFERRED EMBODIMENTS

Figure 1:
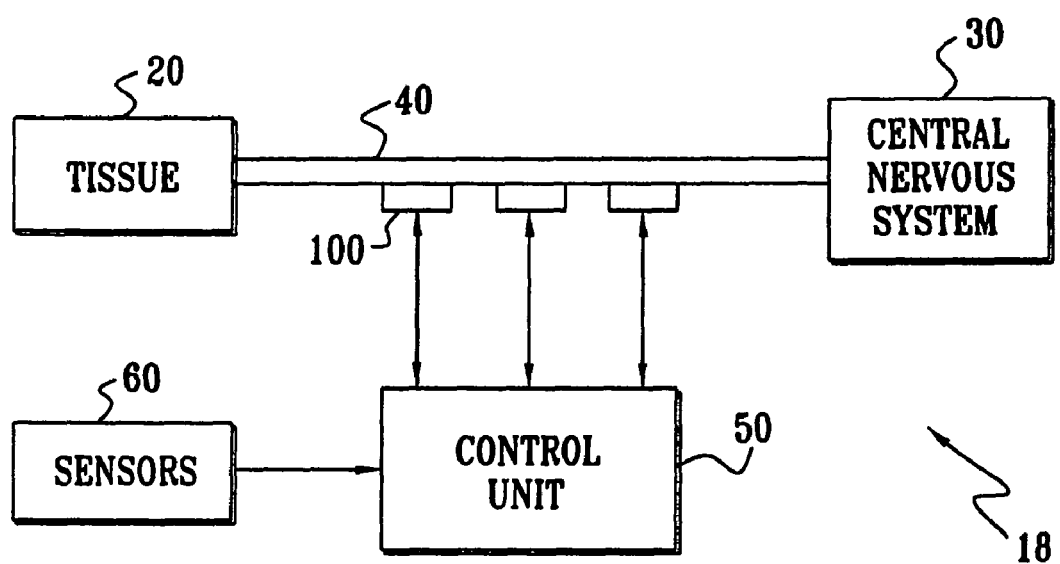
FIG. 1 is a schematic illustration of a nerve, showing the placement of electrode devices thereon, in accordance with a preferred embodiment of the present invention.

FIG. 1 is a schematic illustration of nerve stimulation apparatus 18, for applying electrical energy to induce propagation of impulses in one direction in a nerve 40, in order to treat a condition, while suppressing action potential propagation in the other direction, in accordance with a preferred embodiment of the present invention. For illustrative purposes, nerve 40 may be a cranial nerve, such as the vagus nerve, which emanates from the nervous tissue of the central nervous system (CNS) 30 and transmits sensory signals to CNS 30 and motor or other effector signals to tissue 20. Apparatus 18 typically comprises an implantable or external control unit 50, which drives one or more electrode devices 100 to apply an appropriate signal to respective sites on nerve 40. It is to be understood that whereas preferred embodiments of the present invention are described herein with respect to controlling propagation in a nerve, the scope of the present invention includes applying signals to other nervous tissue, such as individual axons or nerve tracts.

Preferably, control unit 50 receives and analyzes signals from sensors 60 located at selected sites in, on, or near the body of the patient. These sensor signals are typically qualitative and/or quantitative measurements of a medical, psychiatric and/or neurological characteristic of a disorder being treated. For example, sensors 60 may comprise electroencephalographic (EEG) apparatus to detect the onset of a seizure, or a user input unit, adapted to receive an indication of a level of discomfort, hunger, or fatigue experienced by the patient. Preferably, the sensor signals are analyzed within control unit 50, which, responsive to the analysis, drives electrode devices 100 to apply current to one or more sites on nerve 40, configured such that application thereof stimulates unidirectional propagation of nerve impulses to treat the specific disorder of the patient.

Alternatively, nerve stimulation apparatus 18 operates without sensors 60. In such a preferred embodiment, control unit 50 is typically preprogrammed to operate continuously, in accordance with a schedule, or under regulation by an external source.

For some applications of the present invention, the signals applied by control unit 50 to electrode devices 100 are configured to induce efferent nerve impulses (i.e., action potentials propagating in the direction of tissue 20), while suppressing nerve impulses traveling in nerve 40 towards CNS 30. For illustrative purposes, tissue 20 may comprise muscle tissue of the gastrointestinal tract, and treatment of motility disorders may be accomplished by inducing propagation of nerve impulses towards the muscle tissue, while suppressing the propagation of nerve impulses to CNS 30. Preferably, methods and apparatus described in U.S. Pat. No. 5,540,730 to Terry et al. are adapted for use with this embodiment of the present invention. In contrast to the outcome of application of the apparatus described in the Terry patent, however, in this embodiment of the present invention, CNS 30 substantially does not receive sensory signals that could potentially generate undesired responses.

Alternatively or additionally, gastroesophageal reflux disease (GERD) is treated by stimulating the vagus nerve unidirectionally, in order to induce constriction of the lower esophageal sphincter. Advantageously, such an application of unidirectional stimulation inhibits or substantially eliminates undesired sensations or other feedback to the central nervous system which would in some cases be induced responsive to stimulation of the vagus nerve. It is noted that this suppression of afferent impulses is typically only applied during the relatively short time periods during which pulses are applied to the vagus nerve, such that normal, physiological afferent impulses are in general able to travel, uninhibited, towards the CNS. For some applications, apparatus and methods described in the above-cited U.S. Pat. Nos. 5,188,104, 5,716, 385 or 5,423,872 are adapted for use with unidirectional stimulation as provided by this embodiment of the present invention.

For some applications of the present invention, electrode devices 100 are configured to induce afferent impulses (i.e., action potentials propagating in the direction of CNS 30), while suppressing impulses in the direction of tissue 20. Typically, conditions such as eating disorders, coma, epilepsy, motor disorders, sleep disorders, hypertension, and neuropsychiatric disorders are treated by adapting techniques described in one or more of the above-cited references for use with therapeutic unidirectional impulse generation as provided by these embodiments of the present invention. Advantageously, this avoids unwanted and not necessarily beneficial outcomes of the prior art technique, such as bradycardia, enhanced gastric acid secretion, or other effects secondary to stimulation of the vagus nerve and communication of unintended nerve impulses to tissue 20. Which specific tissue 20 receives the efferent stimulation unintentionally induced by the prior art techniques depends upon the location on the nerve at which the stimulation is applied. For example, branchial motor efferents of the vagus nerve supply the voluntary muscles of the pharynx and most of the larynx, as well as one muscle of the tongue. The visceral efferents include parasympathetic innervation of the smooth muscle and glands of the pharynx, larynx, and viscera of the thorax and abdomen. Consequently, unintended efferent signal generation may induce undesired or unexpected responses in any of the tissue controlled and regulated by the vagus nerve. In preferred embodiments of the present invention, by contrast, such responses are suppressed while, at the same time, the desired afferent nerve signals are transmitted to CNS 30.

A variety of methods for inducing unidirectional propagation of action potentials are known in the art, some of which are described in the references cited in the Background section of the present patent application and may be adapted for use with preferred embodiments of the present invention.

In a preferred embodiment, unidirectional signal propagation is induced using methods and apparatus disclosed in:

U.S. Provisional Patent Application 60/263,834 to Cohen and Ayal, filed Jan. 25, 2001, entitled "Selective blocking of nerve fibers," which is assigned to the assignee of the present patent application and is incorporated herein by reference, U.S. patent application Ser. No. 09/824,682, filed Apr. 4, 2001, entitled "Method and apparatus for selective control of nerve fibers," to Cohen and Ayal, which is assigned to the assignee of the present patent application and is incorporated herein by reference, and/or the above-cited U.S. Pat. Nos. 5,199,430, 4,628,942, and/or 4,649,936.

The Cohen and Ayal regular patent application describes a method for:

(a) selectively suppressing the propagation of naturally-generated action potentials which propagate in a predetermined direction at a first conduction velocity through a first group of nerve fibers in a nerve bundle, while (b) avoiding unduly suppressing the propagation of naturally-generated action potentials propagated in the predetermined direction at a different conduction velocity through a second group of nerve fibers in the nerve bundle.

The method includes applying a plurality of electrode devices to the nerve bundle, spaced at intervals along the bundle. Each electrode device is capable of inducing, when actuated, unidirectional "electrode-generated" action potentials, which produce collision blocks with respect to the naturally-generated action potentials propagated through the second group of nerve fibers. Moreover, each electrode device is actuated in sequence, with inter-device delays timed to generally match the first conduction velocity and to thereby produce a wave of anodal blocks, which: (a) minimize undesired blocking of the naturally-generated action potentials propagated through the first group of nerve fibers, while (b) maximizing the generation rate of the unidirectional electrode-generated action potentials which produce collision blocks of the naturally-generated action potentials propagated through the second group of nerve fibers. Such a method may be used for producing collision blocks in sensory nerve fibers in order to suppress pain, and also in motor nerve fibers to suppress selected muscular or glandular activities.

Alternatively or additionally, embodiments of the present invention induce the propagation of unidirectional action potentials using techniques described in the above-cited U.S. Pat. No. 4,649,936 to Ungar et al., and U.S. Pat. No. 4,608,985 to Chrish et al., which describe apparatus and methods for selectively blocking action potentials passing along a nerve trunk. In this case, electrode device 100 comprises an asymmetric, single electrode cuff, which includes an electrically non-conductive or dielectric sleeve that defines an axial passage therethrough. The dielectric sheath and axial passage extend from a first end, which is disposed toward the origin of orthodromic pulses, to a second end. The gap between the nerve and the cuff is filled by conductive body tissues and fluids after implantation in the body. A single annular electrode is disposed in the axial passage, which may be mounted on the inner surface of the dielectric sleeve within the axial passage. Other implementation details may be found in the Ungar and Chrish patents.

According to another aspect of the present invention, there is provided a method of selectively suppressing the propagation of body-generated action potentials propagated in a predetermined direction at a first velocity through a first group of nerve fibers in a nerve bundle without unduly suppressing the propagation of body-generated action potentials propagated in the predetermined direction at a different velocity through a second group of nerve fibers in the nerve bundle, comprising: applying a plurality of electrode devices to, and spaced along the length of, the nerve bundle, each electrode device being capable of outputting, when actuated, unidirectional electrode-generated action potentials producing collision blocks with respect to the body-generated action potentials propagated through the second type of nerve fibers; and sequentially actuating the electrode devices with delays timed to the first velocity to produce a "green wave" of anodal blocks minimizing undesired blocking of the body-generated action potentials propagated through the first group of nerve fibers while maximizing the generation rate of said unidirectional electrode-generated action potentials producing collision blocks with respect to the body-generated action potentials propagated through said second type of nerve fibers.

Such a method may be used for producing collision blocks in sensory nerve fibers in order to suppress pain, and also in motor nerve fibers to suppress selected muscular or glandular activities.

According to a further aspect of the invention, there is provided a method of selectively controlling nerve fibers in a nerve bundle having fibers of different diameters propagating action potentials at velocities corresponding to their respective diameters, comprising: applying a plurality of electrode devices to, and spaced along the length of, the nerve bundle, each electrode device being capable of producing, when actuated, unidirectional electrode-generated action potentials; and sequentially actuating the electrode devices with delays timed to the velocity of propagation of action potentials through the fibers of one of the diameters.

In some described preferred embodiments, the electrode devices are sequentially actuated to generate unidirectional action potentials producing collision blocks of the body-generated action potentials propagated through the nerve fibers of another diameter. Such collision blocks may be used for suppressing pain sensations without unduly interfering with normal sensations, or for selectively suppressing certain motor controls without unduly interfering with others.

A basic element in the preferred embodiments of the method and apparatus described below is the tripolar electrode device. Its construction and operation are diagrammatically illustrated in FIG. 2.

Figure 2:
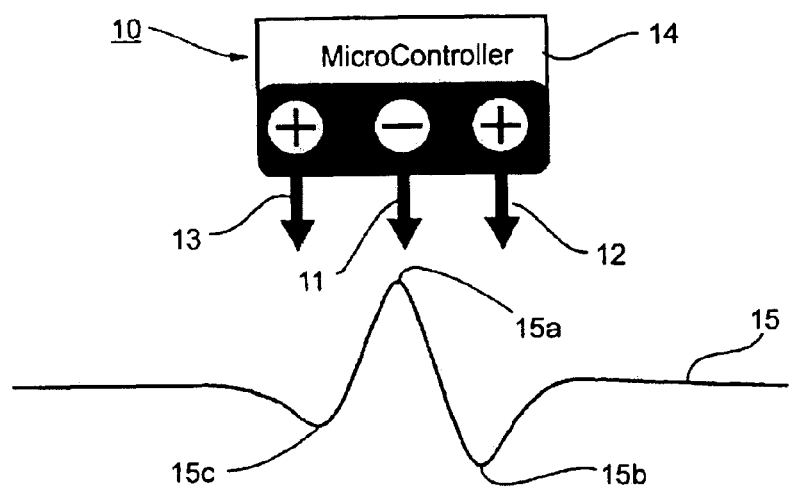
FIG. 2 illustrates the construction and mode of operation of a tripolar electrode device particularly useful in the present invention.

As shown in FIG. 2, the tripolar electrode device, therein designated 10, includes three electrodes, namely, a central cathode 11, a first anode 12 on one side of the cathode, and a second anode 13 on the opposite side of the cathode. The illustrated tripolar electrode device further includes a microcontroller 14 for controlling the three electrodes 11, 12 and 13, as will be described below.

Curve 15 shown in FIG. 2 illustrates the activation function performed by the tripolar electrode device 10 on the nerve bundle underlying it. As shown in FIG. 2, this activation function includes a sharp positive peak 15a underlying the cathode 11, a relatively deep negative dip 15b underlying the anode 12, and a shallower negative dip 15c underlying the anode 13.

When the tripolar electrode 10 is placed with its cathode 11 and anodes 12, 13 in contact with, or closely adjacent to, a nerve bundle, the energization of the cathode 11 generates, by cathodic stimulation, action potentials in the nerve bundle which are propagated in both directions; the energization of anode 12 produces a complete anodal block to the propagation of the so-generated action potentials in one direction; and the energization of anode 13 produces a selective anodal block to the propagation of the action potentials in the opposite direction.

According to another aspect of the present invention, a plurality of electrode devices, preferably of such tripolar electrodes, are used to generate a sequence of electrode-generated action potentials (EGAPs) for more effectively suppressing the propagation of body-generated action potentials (BGAPs) propagated through sensory nerves towards the central nervous system (CNS) for pain control, as well as for suppressing the propagation of body-generated action potentials propagated through motor nerves from the central nervous system towards the peripheral nervous system (PNS) for muscular or glandular stimulation or suppression. As will be described more particularly below, the plurality of electrode devices are sequentially actuated with delays to produce a "green wave" of unidirectional EGAPs effective to reduce the interference with the BGAPs propagated unhindered, or to reinforce the stimulation of muscular or glandular activities desired to be effected.

Figure 3:
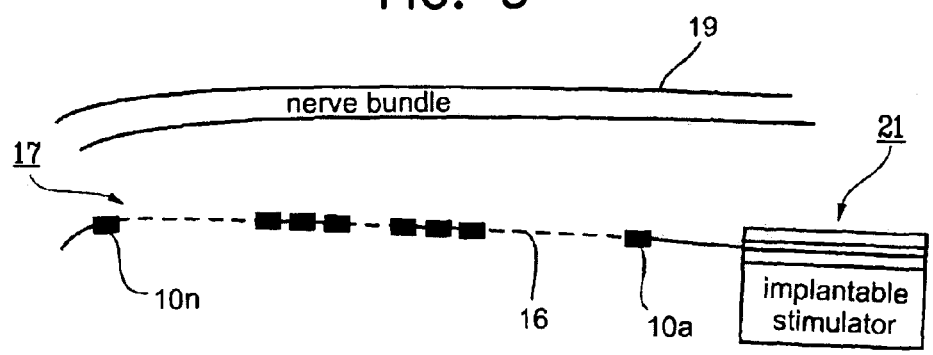
FIG. 3 diagrammatically illustrates an array of tripolar electrode devices constructed in accordance with the present invention for selectively blocking the propagation through certain nerve-fibers of body-generated action potentials.
Figure 4:
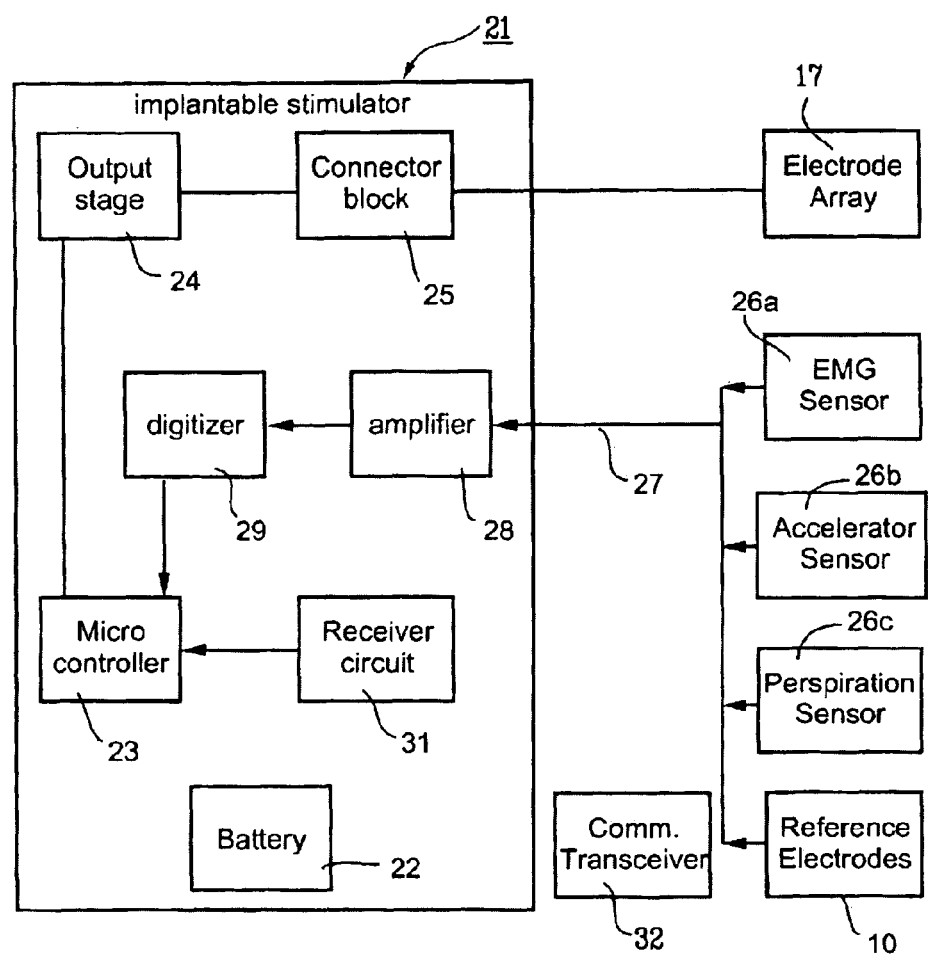
FIG. 4 is a block diagram illustrating the stimulator in the apparatus of FIG. 3.

FIGS. 3 and 4 are diagrams illustrating one form of apparatus constructed in accordance with the present invention utilizing a plurality of the tripolar electrode devices, therein designated 10a-10n, shown in FIG. 2. Such electrode devices are interconnected by a bus 16 to form an electrode array 17 to be applied, as by implantation, with the electrode devices spaced along the length of the nerve bundle, shown at 19, and to be selectively actuated, as will be described more particularly below, by a stimulator, generally designated 21. The construction of the stimulator 21 is more particularly illustrated in FIG. 4.

Each of the electrode devices 10a-10n is of the tripolar construction shown in FIG. 2, to include a central cathode 11 flanked on its opposite sides by two anodes 12, 13. Each such electrode device further includes a microcontroller, shown at 14 in FIG. 2, and more particularly described below with respect to FIG. 8, for sequentially controlling the actuation of the electrodes 11-13 of each electrode device in order to produce the "green wave" briefly described above, and to be more particularly described below.

The assembly of electrode devices 10a-10n, and the stimulator 21 for sequentially actuating them, are preferably both implantable in the body of the subject with the electrodes in contact with, or closely adjacent to, the nerve bundle 15. Accordingly, the simulator 21 includes its own power supply, shown at 22 in FIG. 4. The stimulator 21 further includes a microcontroller 23 having output stage 24 connected, via connector block 25, to the plurality of electrode devices 10a-10n for sequentially actuating them, as will be described below.

Stimulator 21 further includes an input circuit for inputting various sensor signals for purposes of calibration and/or control. As shown in FIG. 4, such inputs may be from an EMG (electromyogram) signal sensor 26a and from an accelerator sensor 26b. The EMG sensor 26a may be used for calibration purposes, e.g., to calibrate the apparatus according to EMG signals generated by a subject's muscle during the calibration of the apparatus (described below), or for control purposes, e.g., for automatically actuating the device upon the occurrence of a particular EMG signal. The accelerator sensor 26b may be used for control purposes, e.g., to automatically actuate the device upon the occurrence of tremors or spasms in order to suppress in the tremors by blocking certain motor nerves.

Stimulator 21 may also have an input from a perspiration sensor 26c for automatic control of sweat glands. It may also have an input from one of the electrodes serving as a reference electrode for calibration purposes, as will also be described more particularly below.

The inputs into the stimulator 21 may be by wire or bus, as shown at 27 in FIG. 4. Such inputs are amplified in amplifier 28, and digitized in a digitizer 29, before being inputted into the microcontroller 23.

The inputs to the stimulator 21 may also be by wireless communication, as schematically shown at 32 in FIG. 4, particularly where the device is implanted. For this purpose, stimulator 21 includes a receiver 31 for receiving such inputs. Such inputs are also amplified in amplifier 28 and digitized in digitizer 29 before being inputted into the microcontroller 23.

Operation of the Illustrated Apparatus

The apparatus illustrated in FIGS. 3 and 4, when applied along the length of the nerve bundle 15 as shown in FIG. 3, is capable of suppressing the propagation of body-generated action potentials (BGAPs) propagated through the small-diameter nerve fibers in a nerve bundle without unduly suppressing the propagation of BGAPs propagated through the large-diameter nerve fibers in the nerve bundle. One application of such a device is to reduce pain sensations; and another application of the device is to suppress muscular or glandular activities. The apparatus illustrated in FIGS. 3 and 4 may also be used for generating, by the electrode devices, action potentials (hereinafter frequently referred to as electrode-generated action potentials, or EGAPS) where the body fails to produce the necessary BGAPs to produce a particular muscular or glandular activity. A further application of the apparatus, therefore, is to stimulate a muscular or glandular activity.

As described above, when the cathode 11 of each tripolar electrode device 10 is actuated, it generates an action potential by cathodic stimulation propagated in both directions; whereas when anode 12 of the respective tripolar electrode 10 is energized, it produces a complete anodal block on one side of the cathode, to thereby make the electrode-generated action potential unidirectional and propagated away from the central nervous system. On the other hand, when anode 13 is energized, it produces an anodal block only with respect to the BGAPs propagated through the large-diameter sensory nerves, since they are more sensitive to the anodal current. Accordingly, the EGAPs from the small-diameter sensory nerves are permitted, to a larger extent, to propagate through the anodal block.

The EGAPs outputted by the anodal block may be used as collision blocks with respect to sensory BGAPs to suppress pain, or with respect to motor BGAPs to suppress undesired muscular activity (e.g., tremors, spasms), or glandular activity (e.g., excessive perspiration).

An undesired side effect of this activation scheme, is that at the time when anode 12 of device 10 is actuated to generate an anodal block as described above, all BGAPs in both small and large fibers are blocked and cannot pass the device. Thus every production of an EGAP is accompanied by a brief period in which all BGAPs cannot pass the site of the device 10. In order to minimize the blocking of BGAPs while maximizing the amount of EGAPs produced, the tripolar electrode devices 10a-10n are sequentially actuated, under the control of the stimulator 21. This sequential actuation is timed with the propagation velocity of the action potentials through the nerve fiber not to be blocked. Thus, as well known for controlling vehicular traffic, when stop lights spaced along a thoroughfare are controlled to define a "green wave" travelling at a predetermined velocity, the vehicles travelling at the "green wave" velocity will be less hindered than if the stop lights were not synchronized with their velocity.

The anodal blocks produced by the sequential actuation of the tripolar electrodes are comparable to the stop lights in a thoroughfare, and therefore the action potentials travelling at the velocity of the green wave will be less hindered by such stop lights or anodal blocks.

Thus, where the invention is used for pain control by suppressing the BGAPs in the small-diameter sensory nerves, producing a "green wave" of anodal blocks timed with the conduction velocity through the large-diameter sensory nerves, there will be less interference with the BGAPs representing normal sensations, travelling through the large-diameter sensory nerve fibers, as compared to the BGAPs representing pain sensations travelling through the small-diameter sensory nerve fibers which will be collision blocked by the EGAPs.

The same "green wave" effect can be provided in order to suppress BGAPs propagating through motor nerve fibers in order to block motor controls of selected muscles or glands.

Examples of Use of the Apparatus

Figure 5:
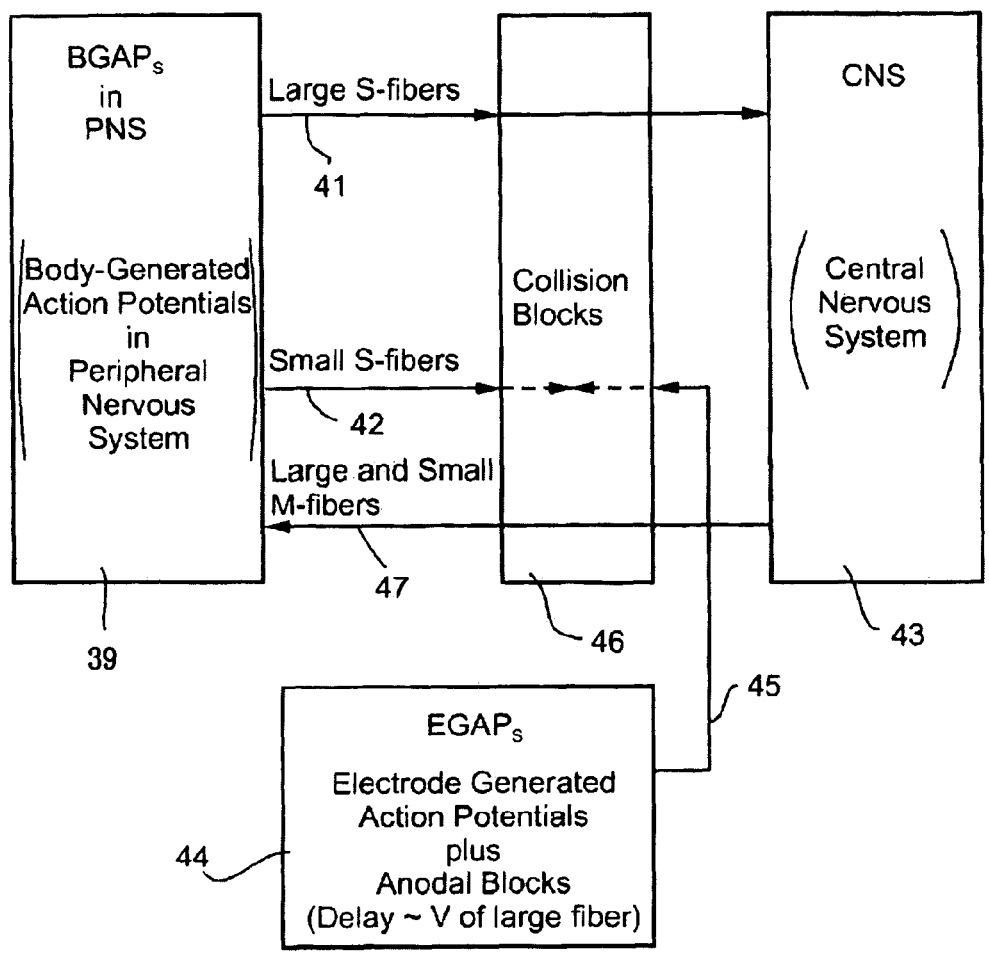
FIG. 5 is a block diagram illustrating the operation of the apparatus of FIGS. 3 and 4 for suppressing pain sensations.

FIG. 5 illustrates an example of use of the described apparatus for reducing pain sensations by suppressing the BGAPs transmitted through the small-diameter sensory fibers without unduly hindering the transmission of the BGAPs through the large-diameter sensory fibers.

Thus, as shown in FIG. 5, the BGAPs in the peripheral nervous system PNS (block 39) generate normal sensations in the large sensory fibers 41 and pain sensations in the small sensory fibers 42. Normally, both types of sensations are propagated through their respective fibers to the central nervous system (CNS, block 43).

However, as shown in FIG. 5, the assembly of electrodes 10a-10n, when sequentially actuated with delays timed to the conduction velocity of the large-diameter fibers 41, generates unidirectional EGAPs (block 44) which are outputted with delays timed to correspond to the velocity of the large sensory fibers (as shown at 45) to produce a collision block (46) with respect to the BGAPs propagated through the small sensory fibers (42) without unduly hindering the BGAPs propagated through the large sensory fibers 41 to the central nervous system 43. Accordingly, the pain sensations normally propagated through the small sensory fibers 42 to the central nervous system 43 will be suppressed, while the normal sensations propagated through the large sensory fibers 41 will continue substantially unhindered to the central nervous system.

In addition, as shown by line 47 in FIG. 5, the motor action potentials from the CNS to the PNS are also substantially unhindered.

Figure 6A:
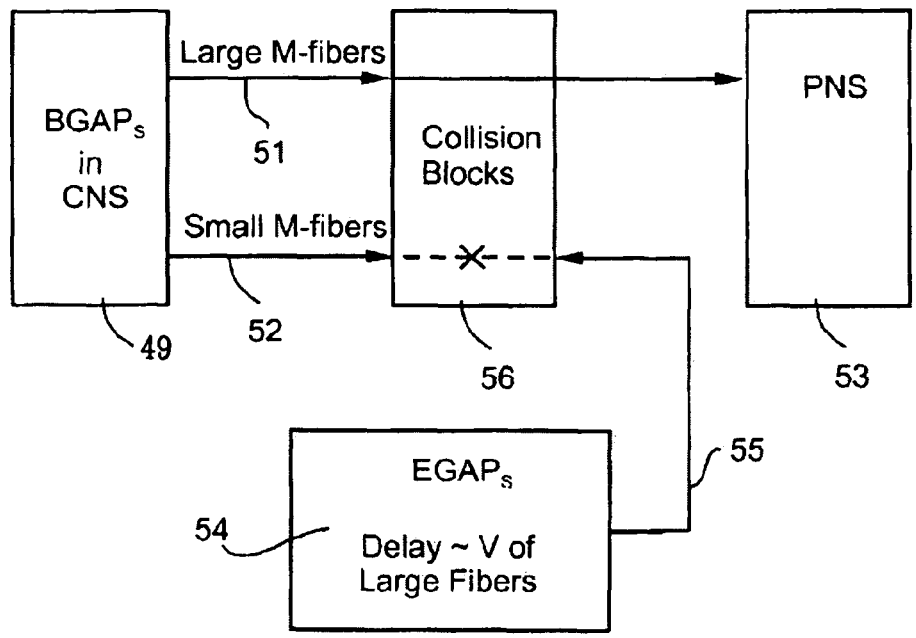
FIGS. 6A and 6B are block diagrams illustrating how the apparatus of FIGS. 3 and 4 may also be used for suppressing selected muscular or glandular activities controlled by the motor nerves.
Figure 6B:
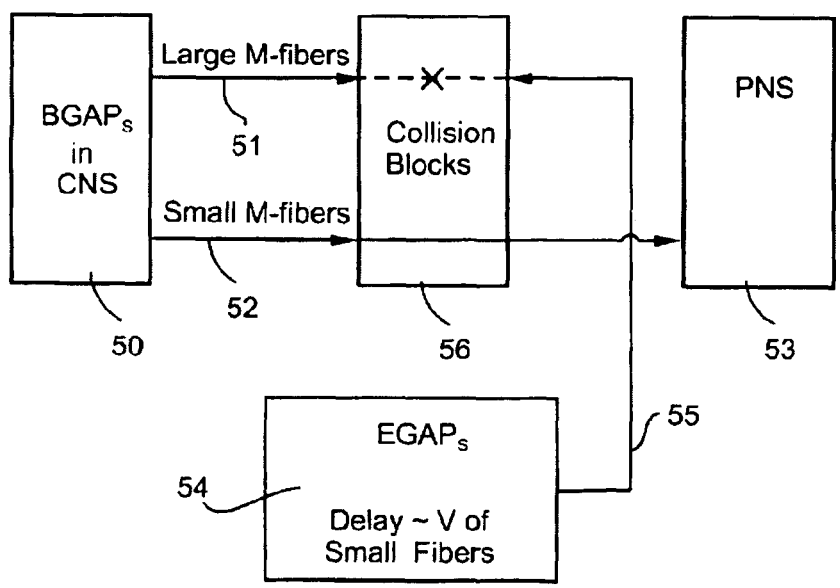

FIGS. 6A and 6B illustrate the application of the apparatus for suppressing certain muscular or glandular activities normally controlled by the BGAPs transmitted through the motor nerve fibers. In this case, as shown in FIG. 6A, the BGAPs are generated in the central nervous system (block 49) and are normally transmitted via large motor fibers 51 and small motor fibers 52 to the peripheral nervous system 53. FIG. 6B illustrates the arrangement wherein the EGAPs are generated at a rate corresponding to the velocity of the large motor fibers, as shown by blocks 54 and 55, so that they produce collision blocks with respect to the small motor fibers 52, and permit the BGAPs to be transmitted through the large motor fibers 51 to the peripheral nervous system 53.

FIG. 6B illustrates the variation wherein the apparatus generates EGAPs at a rate corresponding to the velocity of the small motor fibers (blocks 54, 55), such that the collision blocks (56) block the large motor fibers 51, and permit the BGAPs to be transmitted to the peripheral nervous system 53.

Figure 7A:
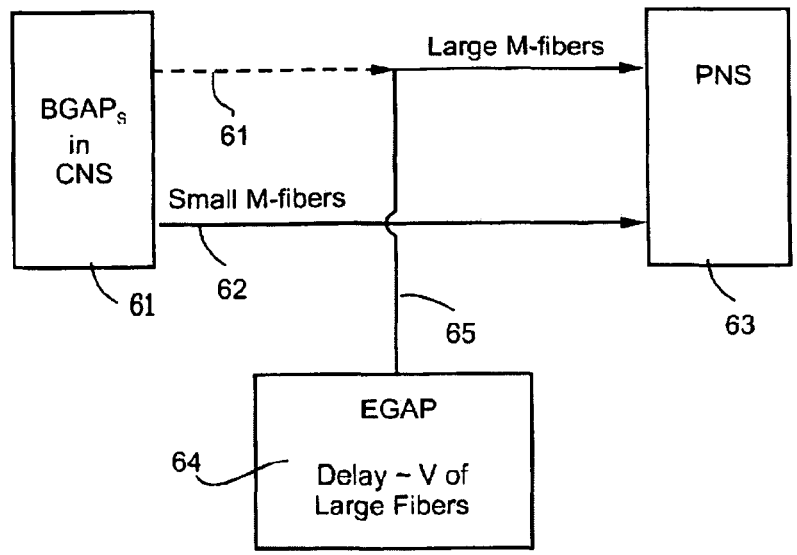
FIGS. 7A and 7B are block diagrams illustrating how the apparatus of FIGS. 3 and 4 may also be used for stimulating selected motor or glandular activities upon the failure of the body to generate the required action potentials.
Figure 7B:
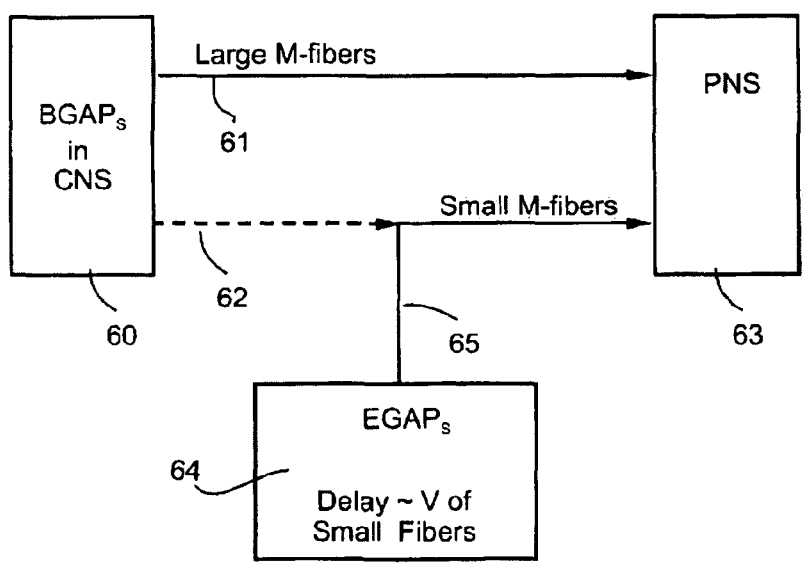

FIGS. 7A and 7B illustrate the applications of the apparatus for stimulating a particular muscle or gland where the body fails to develop adequate BGAPs in the respective motor nerve fiber for the respective muscular or glandular control. In this case, the apparatus generates unidirectional EGAPs selectively for the respective muscle or gland.

FIG. 7A illustrates the application of the invention wherein the body fails to generate in the central nervous system 61 adequate BGAPs for transmission by the large motor fibers to the peripheral nervous system 63, in which case the electrode devices 10a-10n in the electrode assembly would be sequentially energized by the stimulator 64 with delays timed to the velocity of propagation of action potentials through the large motor fibers. The unidirectional EGAPs are thus produced with delays timed to the conductive velocity of the large motor fibers, thereby permitting them to be transmitted via the large motor fibers to the peripheral nervous system.

FIG. 7B, on the other hand, illustrates the case where the electrodes 10a-10n are sequentially energized with delays timed to the velocity of the small motor fibers, thereby permitting the unidirectional EGAPs to be outputted via the small-diameter fibers to the peripheral nervous system 63.

Calibration

For best results, each electrode assembly should be calibrated for each patient and at frequent intervals. Each calibration requires adjustment of the cathodic and anodic currents in each tripolar electrode, and also adjustment of the timing of the sequential actuation of the tripolar electrodes.

To calibrate the cathodic and anodic currents for each electrode, the proximal electrode (10a, FIG. 3) is actuated to produce a unidirectional action potential propagated towards the distal electrode (10n) at the opposite end of the array. The so-produced action potential, after having traversed all the electrodes between electrodes 10a, and 10n, is detected and recorded by the distal electrode 10n. The currents in the electrodes are iteratively adjusted to produce maximum blocking.

Figure 8A:
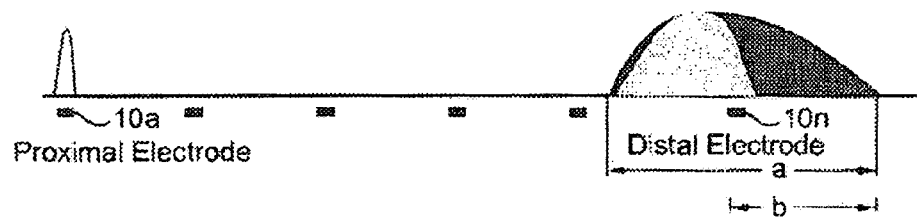
FIGS. 8A and 8B are diagrams helpful in explaining the manner of calibrating the apparatus of FIGS. 3 and 4.

FIG. 8A illustrates, at "a", the signal detected by the distal electrode when the blocking is minimum, and at "b" when the signal detected by the distal electrode when the blocking is maximum.

Figure 8B:
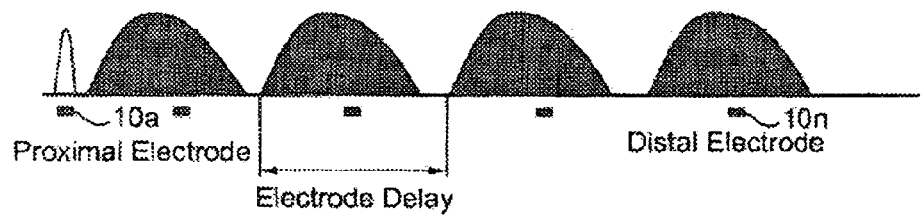

FIG. 8B illustrates the manner of calibrating the electrode array to produce the proper timing in the sequential actuation of the electrodes for calibrating the sequential timing, the proximate electrode (10a) is again actuated to produce a unidirectional action potential propagated toward the distal electrode (10n). As the so-produced action potential traverses all the electrodes inbetween, each such inbetween electrode detects and records the action. This technique thus enables calibrating the electrode array to produce the exact delay between the actuations of adjacent electrodes to time the sequential actuations with the conduction velocity of the respective nerve fiber.

For example, where the sequential actuation is to produce a "green wave" having a velocity corresponding to the conduction velocity of the large sensory nerve fibers for reducing pain sensations, the timing would be adjusted so as to produce the sequential delay shown in FIG. 8B to thereby time the sequential actuations of the electrodes to the conductive velocity in the large sensory fibers.

The EMG sensor 26a shown in FIG. 4 may also be used for calibrating the electrode currents and sequential timing when the apparatus is to be used for providing a stimulation of a muscular or glandular activity where the body fails to provide the necessary BGAPs for this purpose. In this case, the currents and timing would be adjusted to produce a maximum output signal from the EMG sensor 26a for the respective muscle.

The EMG sensor 26a could also be used to automatically actuate the apparatus upon the detection of an undesired EMG signal, e.g., as a result of a tremor or spasm to be suppressed. For example, the accelerator sensor 26b could be attached to a limb of the subject so as to automatically actuate the apparatus in order to suppress tremors in the limb upon detection by the accelerator.

Other sensors could be included, such as an excessive perspiration sensor 26c, FIG. 4. This would also automatically actuate the apparatus to suppress the activity of the sweat glands upon the detection of excessive perspiration.

A method is provided of reducing pain sensations resulting from the propagation of body-generated action potentials towards the central nervous system through small-diameter sensory fibers in a nerve bundle, without unduly reducing other sensations resulting from the propagation of body-generated action potentials towards the central nervous system through large-diameter sensory fibers in the nerve bundle, comprising: applying to the nerve bundle at least one electrode device capable, upon actuation, of generating unidirectional action potentials to be propagated through both the small-diameter and large-diameter sensory fibers in the nerve bundle away from the central nervous system; and actuating the electrode device to generate the unidirectional action potentials to produce collision blocks with respect to the body-generated action potentials propagated through the small-diameter fibers.

The electrode device may include electrodes which:
(i) generate the electrode-generated action potentials by cathodic stimulation;
(ii) produce a complete anodal block on one side of the cathode to make the electrode-generated action potentials unidirectional; and
(iii) produce a selective anodal block on the opposite side of the cathode to cause the electrode-generated action potentials to produce collision blocks with respect to the body-generated action potentials propagated through the small-diameter sensory fibers.

The electrode device may be a tripolar electrode device which includes a central cathode for producing the cathodic stimulation, a first anode on one side of the cathode for producing the complete anodal block, and a second anode on the opposite side of the cathode for producing the selective anodal block. There may be a plurality of the electrode devices spaced along the length of the nerve bundle; and wherein the electrode devices are sequentially actuated with delays timed to the velocity of propagation of the body-generated action potentials through the large-diameter fibers to produce a "green wave" of electrode-generated anodal blocks, thereby increasing the number of EGAPs in the small diameter fibers producing collision blocks while minimizing anodal blocking of the BGAPs propagated through the large-diameter sensory fibers.

A method is provided of selectively suppressing the propagation of body-generated action potentials propagated in a predetermined direction at a first velocity through a first group of nerve fibers in a nerve bundle without unduly suppressing the propagation of body-generated action potentials propagated in the predetermined direction at a different velocity through a second group of nerve fibers in the nerve bundle, comprising: applying a plurality of electrode devices to, and spaced along the length of, the nerve bundle, each electrode device being capable of outputting, when actuated, unidirectional electrode-generated action potentials producing collision blocks with respect to the body-generated action potentials propagated through the second type of nerve fibers; and sequentially actuating the electrode devices with delays timed to the first velocity to produce a "green wave" of anodal blocks minimizing undesired blocking of the body-generated action potentials propagated through the first group of nerve fibers, while maximizing the generation rate of the unidirectional electrode-generated action potentials producing collision blocks with respect to the body-generated action potentials propagated through the second type of nerve fibers.

The first group of nerve fibers may be large-diameter nerve fibers; and the second group of nerve fibers are small-diameter nerve fibers. The nerve fibers may be sensory nerve fibers, in which the predetermined direction of propagation of the body-generated action potentials to be collision blocked is towards the central nervous system, the method being effective for suppressing pain sensations propagated through the small-diameter sensory fibers without unduly suppressing other sensations propagated through the large-diameter sensory fibers.

The nerve fibers may be motor nerve fibers in which the predetermined direction of propagation of the body-generated action potentials to be collision blocked is away from the central nervous system towards a muscle or gland, the method being effective for suppressing motor impulses propagated through the small-diameter motor nerve fibers without unduly suppressing the propagation of the motor impulses through the large-diameter motor nerve fibers.

Each of the electrode devices may be a tripolar electrode which includes a central cathode for producing the electrode-generated action potentials by cathodic stimulation, a first anode on one side of the cathode for making the electrode-generated action potentials unidirectional, and a second anode on the opposite side of the cathode for producing the selective anodal blocking of the electrode-generated action potentials.

A method is provided of selectively controlling nerve fibers in a nerve bundle having fibers of different diameters propagating action potentials at velocities corresponding to their respective diameters, comprising: applying a plurality of electrode devices to, and spaced along the length of, the nerve bundle, each electrode device being capable of producing, when actuated, unidirectional electrode-generated action potentials; and sequentially actuating the electrode devices with delays timed to the velocity of propagation of action potentials through the fibers of one of the diameters.

The electrode devices may be sequentially actuated to generate unidirectional action potentials producing collision blocks of the body-generated action potentials propagated through the nerve fibers of a another diameter. The electrode devices may be sequentially actuated with delays timed to the velocity of the larger-diameter nerve fibers to produce a "green-wave" of anodal blocks in order to minimize blocking the body-generated action potentials propagated through the larger-diameter fibers while maximizing the number of EGAPs collision blocking the body-generated action potentials propagated through the small diameter fibers. The fibers may include large-diameter sensory fibers propagating body-generated action potentials representing normal sensations from the peripheral nervous system to the sensor nervous system, and small-diameter sensory fibers propagating body-generated action potentials representing pain sensations from the peripheral nervous system to the central nervous system, which pain sensations in the small-diameter sensory fibers are suppressed by collision block and the "green-wave" of anodal blocks minimizes blocking of the normal sensations in the large-diameter sensory nerves. The nerve fibers may include large-diameter motor fibers propagating body-generated action potentials representing certain motor controls from the central nervous system to the peripheral nervous system, and small-diameter motor nerve fibers representing other motor controls from the central nervous system to the peripheral nervous system, the motor controls in the small-diameter motor fibers being suppressed by collision blocks and the green-wave of anodal blocks minimizes blocking of the motor controls in the large-diameter motor fibers.

The nerve fibers may be motor fibers of different diameters for propagating body-generated action potentials from the central nervous system to the peripheral nervous system, the electrode devices being sequentially actuated to generate unidirectional action potentials to serve as motor action potentials to be propagated from the central nervous system to the peripheral nervous system to replace motor action potentials failed to be generated by the body.

Each of the electrode devices may be a tripolar electrode which includes a central cathode for producing the electrode-generated action potentials by cathodic stimulation, a first anode on one side of the cathode for making the electrode-generated action potentials unidirectional, and a second anode on the opposite side of the cathode for producing the selective anodal blocking of the electrode-generated action potentials.

Apparatus is provided for selectively blocking pain sensations resulting from the propagation of body-generated action potentials towards the central nervous system through small-diameter sensory fibers in a nerve bundle, without unduly reducing other sensations resulting from the propagation of body-generated action potentials towards the central nervous system through large-diameter sensory fibers in the nerve bundle, comprising:

an electrical device to be applied to the nerve bundle and having at least one electrode device capable, upon actuation, of generating unidirectional action potentials to be propagated through both the small-diameter and large-diameter sensory fibers in the nerve bundle away from the central nervous system;

and a stimulator for actuating the electrode device to generate the unidirectional action potentials to produce collision blocks of the body-generated action potentials in the small-diameter sensory fibers.

The electrode device may include electrodes which:
(a) generate the electrode-generated action potentials by cathodic stimulation;
(b) produce a complete anodal block on one side of the cathode to make the electrode-generated action potentials unidirectional; and
(c) produce a selective anodal block on the opposite side of the cathode to block the electrode-generated action potentials propagated through the large-diameter sensory fibers to a greater extent than those propagated through the small-diameter sensory fibers.

The electrode device may be a tripolar electrode which includes a central cathode for producing the cathodic stimulation, a first anode on one side of the cathode for producing the complete anodal block, and a second anode on the opposite side of the cathode for producing the selective anodal block. There may be a plurality of the electrode devices spaced along the length of the nerve bundle; and wherein the electrode devices are sequentially actuated with delays corresponding to the velocity of propagation of the body-generated action potentials through the large-diameter fibers to produce a "green wave" of electrode-generated action potentials collision blocking with the body-generated action potentials propagated through the small-diameter fibers while minimizing anodal blocking of action potentials propagating through the large-diameter fibers.

Apparatus is provided for selectively suppressing the propagation of body-generated action potentials propagated at a first velocity through a first type of nerve fibers in a nerve bundle without unduly suppressing the propagation of body-generated action potentials propagated at a different velocity through a second type of nerve fibers in the nerve bundle, comprising: spacing a plurality of electrodes to be spaced along the length of the nerve bundle, each capable of producing, when actuated, unidirectional electrode-generated action potentials and a selective anodal block of the latter action potentials propagated through the first type of nerve fibers to a greater extent than those propagated through the second type of nerve fibers; and a stimulator for sequentially actuating the electrode devices with delays timed to the first velocity to produce a "green wave" of anodal blocks minimizing undesired blocking of the body-generated action potentials propagated through the first group of nerve fibers, while maximizing the generation rate of the unidirectional electrode-generated action potentials producing collision blocks with respect to the body-generated action potentials propagated through the second type of nerve fibers.

Each of the electrode devices may be a tripolar electrode which includes a central cathode for producing the electrode-generated action potentials by cathodic stimulation, a first anode on one side of the cathode for making the electrode-generated action potentials unidirectional, and a second anode on the opposite side of the cathode for producing the selective anodal blocking of the electrode-generated action potentials. The plurality of electrode devices and the stimulator may be constructed to be implanted into the subject's body with the electrodes in contact with or closely adjacent to the nerve bundle.

The stimulator may be connected to the plurality of electrode devices by an asynchronous, serial four-wire bus. The stimulator may communicate with the plurality of electrode devices via a wireless communication link. Each of the tripolar electrode devices may include an insulating base carrying the cathode and two anodes on one face thereof, and control circuitry on the opposite face. The control circuitry may include a microprocessor communicating with the stimulator, and an L-C pulsing network controlled by the microprocessor.

Apparatus is provided for selectively controlling nerve fibers in a nerve bundle having fibers of different diameters propagating action potentials at velocities corresponding to their respective diameters, comprising: a plurality of electrode devices to be applied to, and spaced along the length of, the nerve bundle, each electrode device being capable of producing, when actuated, unidirectional electrode-generated action potentials; and a stimulator for sequentially actuating the electrode devices with delays timed to the velocity of propagation of action potentials through the fibers of one of the diameters.

The stimulator may sequentially actuate the electrode devices to generate unidirectional action potentials producing collision blocks of the body-generated action potentials propagated through the nerve fibers of a another diameter. The stimulator may sequentially actuate the electrode devices with delays corresponding to the velocity of larger-diameter nerve fibers to produce a "green-wave" of anodal blocks minimizing undesired blocking of the body-generated action potentials propagated through the large-diameter nerve fibers, while maximizing the generation rate of the unidirectional electrode-generated action potentials producing collision blocks with respect to the body-generated action potentials propagated through the small diameter nerve fibers.

The nerve fibers may be motor fibers of different diameters for propagating body-generated action potentials from the central nervous system to the peripheral nervous system, and the stimulator may sequentially actuate the electrode devices to generate unidirectional action potentials to serve as motor action potentials to be propagated from the central nervous system to the peripheral nervous system to replace motor action potentials failed to be generated by the body.

It is to be understood that whereas preferred embodiments of the present invention are generally described hereinabove with respect to stimulating and inhibiting action potential propagation in the vagus nerve, the scope of the present invention includes applying analogous techniques to other central or peripheral nervous tissue of a patient.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a condition of a subject, comprising:
   a plurality of electrode devices, configured to be coupled to respective longitudinal sites of longitudinal nervous tissue of the subject having first and second types of nerve fibers, through which body-generated action potentials propagate at first and second velocities, respectively, wherein two of the plurality of electrode devices are configured to be coupled at adjacent ones of the longitudinal sites that are separated by at least 2 mm; and
   a control unit, configured to:
   sequentially drive the electrode devices to apply to the nervous tissue respective currents, with delays between driving each of the electrode devices that are timed to the first velocity of the propagation of the body-generated action potentials so as to minimize undesired blocking of the body-generated action potentials propagating through the first type of nerve fibers,
   configure the currents to induce respective first orthodromic electrode-generated action potentials that propagate in the nervous tissue in a first direction, so as to treat the condition,
   configure the currents to suppress respective second electrode-generated action potentials from propagating in the nervous tissue in a second direction opposite to the first direction, repeatedly, during a series of temporally non-contiguous periods, induce the first orthodromic electrode-generated action potentials and suppress the second electrode-generated action potentials, and
   substantially withhold, during respective times between the non-contiguous periods, the inducing of the first orthodromic electrode-generated action potentials and the suppressing of the second electrode-generated action potentials.

2. Apparatus according to claim 1, wherein the control unit is configured to drive the electrode devices to configure the currents to induce the first orthodromic electrode-generated action potentials to propagate in the nervous tissue in an afferent direction with respect to a central nervous system of the subject, so as to treat the condition.

3. Apparatus according to claim 2, wherein the longitudinal tissue includes a vagus nerve of the subject, and wherein the electrode devices are configured to be coupled to the vagus nerve of the subject.

4. Apparatus according to claim 1, wherein the control unit is configured to drive the electrode devices to configure the currents to induce the first orthodromic electrode-generated action potentials to propagate in the nervous tissue in an efferent direction with respect to a central nervous system of the subject, so as to treat the condition.

5. Apparatus according to claim 4, wherein the longitudinal tissue includes a vagus nerve of the subject, and wherein the electrode devices are configured to be coupled to the vagus nerve of the subject.

6. Apparatus according to claim 1, wherein the control unit is configured to: (a) drive the electrode devices to apply the currents, and (b) suppress the second electrode-generated action potentials, at substantially the same time.

7. Apparatus according to claim 1, wherein the control unit is adapted to configure the currents to be capable of treating an involuntary movement disorder of the subject.

8. Apparatus according to claim 1, wherein the control unit is configured to regulate the suppressing of the second electrode-generated action potentials so as to inhibit an undesired response of a central nervous system of the subject generated responsive to the electrode devices applying the currents to the nervous tissue.

9. Apparatus according to claim 1, wherein the control unit is configured to regulate the suppressing of the second electrode-generated action potentials so as to inhibit an undesired sensation generated responsive to the electrode devices applying the currents to the nervous tissue.

10. Apparatus according to claim 1, wherein the control unit is configured to regulate the suppressing of the second electrode-generated action potentials so as to suppress second action potentials induced responsive to the electrode devices applying the currents.

11. Apparatus according to claim 1, wherein the control unit is adapted to configure the currents so as to be capable of treating a sleep disorder of the subject.

12. Apparatus according to claim 1, wherein the control unit is adapted to configure the currents so as to be capable of treating a gastrointestinal motility disorder of the subject.

13. Apparatus according to claim 1, wherein the control unit is adapted to configure the currents so as to be capable of treating an eating disorder of the subject.

14. Apparatus according to claim 1, wherein the control unit is adapted to configure the currents so as to be capable of treating obesity of the subject.

15. Apparatus according to claim 1, wherein the control unit is adapted to configure the currents so as to be capable of treating anorexia of the subject.

16. Apparatus according to claim 1, wherein the control unit is adapted to configure the currents so as to be capable of treating a gastrointestinal tract disorder of the subject.

17. Apparatus according to claim 1, wherein the control unit is adapted to configure the currents so as to be capable of treating hypertension of the subject.

18. Apparatus according to claim 1, wherein the control unit is adapted to configure the currents so as to be capable of treating coma of the subject.

19. Apparatus according to claim 1, wherein the control unit is adapted to configure the currents so as to be capable of treating epilepsy of the subject.

20. Apparatus according to claim 1, wherein the longitudinal tissue includes a vagus nerve of the subject, and wherein the electrode devices are configured to be coupled to the vagus nerve of the subject, and wherein the control unit is configured to: (a) configure the currents so as to be capable of treating epilepsy of the subject, and (b) suppress second electrode-generated action potentials that interfere with an ability of the subject to speak.

21. Apparatus according to claim 1, wherein the longitudinal tissue includes a vagus nerve of the subject, and wherein the electrode devices are configured to be coupled to the vagus nerve of the subject, and wherein the control unit is adapted to configure the currents so as to be capable of inducing constriction of a lower esophageal sphincter of the subject.

22. Apparatus according to claim 1, wherein the electrode devices are configured to be coupled to longitudinal nervous tissue of a central nervous system of the subject.

23. Apparatus according to claim 1, wherein the electrode devices are configured to be coupled to nervous tissue of a peripheral nervous system of the subject.

24. Apparatus according to claim 1, wherein the control unit is configured to regulate the suppressing of the second electrode-generated action potentials so as to inhibit an undesired effector action responsive to driving the electrode devices to apply the currents to the nervous tissue.

25. Apparatus according to claim 24, wherein the control unit is configured to suppress second electrode-generated action potentials that induce increased acid secretion in a gastrointestinal tract of the subject.

26. Apparatus according to claim 24, wherein the control unit is configured to suppress second electrode-generated action potentials that induce muscular contraction.

27. Apparatus according to claim 24, wherein the control unit is configured to suppress second electrode-generated action potentials that induce bradycardia.

28. Apparatus according to claim 1, wherein the control unit is configured to drive the electrode devices to apply respective electric fields to the nervous tissue configured to suppress the second electrode-generated action potentials.

29. Apparatus according to claim 1, wherein two of the plurality of electrode devices are adapted to be coupled at adjacent ones of the sites that are separated by less than 4 mm.

30. Apparatus according to claim 1, and comprising a sensor adapted to sense an indication of a presence of the condition and to generate a sensor signal responsive thereto, wherein the control unit is adapted to drive the electrode devices responsive to the sensor signal.

31. Apparatus according to claim 30, wherein the sensor is configured to sense the indication by sensing at least one physiological parameter of the subject selected from the group consisting of:
electroencephalographic (EEG) waves, respiration changes, heart rate changes, an aura, and a motor effect.

32. Apparatus according to claim 30, wherein the condition includes a gastrointestinal motility disorder of the subject, and wherein the sensor is configured to sense the indication by sensing at least one physiological parameter of the subject selected from the group consisting of: a pattern of contractions of a portion of a gastrointestinal tract of the subject, and digestion by the subject.

33. Apparatus according to claim 30, wherein the condition includes a sleep disorder of the subject, and wherein the sensor is configured to sense the indication by sensing at least one physiological parameter of the subject selected from the group consisting of: a respiration pattern of the subject indicative of wakefulness during normal nocturnal hours, abdominal impedance changes associated with respiration by the subject indicative of the sleep disorder, a sustained abnormal period of cessation of respiration of the subject, respiration typically associated with a state of sleeplessness of the subject, electroencephalographic (EEG) activity of the subject, a sudden uncontrolled nodding of the head of the subject, abdominal impedance of the subject, and eye movement of the subject.

34. Apparatus according to claim 30, wherein the indication includes swallowing by the subject, and wherein the sensor comprises one or more electrodes configured to be implanted in a vicinity of an esophagus of the subject, and to detect the swallowing.

35. Apparatus according to claim 30, wherein the condition includes an eating disorder of the subject, and wherein the indication includes a quantity of food consumed by the subject in a predetermined period of time, and wherein the sensor is configured to sense the quantity.

36. Apparatus according to claim 30, wherein the condition includes an eating disorder of the subject, and wherein the indication includes an amount of food in a stomach of the subject, and wherein the sensor comprises one or more electrodes configured to be secured to an outer wall of the stomach, and to sense the amount of the food in the stomach.

37. Apparatus according to claim 30, wherein the sensor is configured to sense the indication by sensing electroencephalographic (EEG) activity of the subject.

38. Apparatus according to claim 30, wherein the sensor is configured to sense the indication by sensing blood pressure of the subject.

39. Apparatus according to claim 1, wherein the control unit is adapted to receive an input from the subject and to drive the electrode devices responsive to the input.

40. Apparatus according to claim 1, wherein the control unit is adapted to configure the currents so as to be capable of treating migraine headache of the subject.

41. Apparatus according to claim 1, wherein the control unit is adapted to configure the currents so as to be capable of treating depression of the subject.

42. Apparatus according to claim 1, wherein the control unit is adapted to configure the currents so as to be capable of treating tremor of the subject.

43. Apparatus according to claim 1, wherein the control unit is adapted to configure the currents so as to be capable of treating Parkinson's disease of the subject.

44. Apparatus according to claim 1, wherein the control unit is adapted to configure the currents so as to be capable of treating stroke of the subject.

45. Apparatus for treating a condition of a subject, comprising:
a plurality of electrode devices, configured to be coupled to respective longitudinal sites of longitudinal nervous tissue of the subject having first and second types of nerve fibers, through which body-generated action potentials propagate at first and second velocities, respectively;
a sensor, configured to sense an indication of a presence of the condition and to generate a sensor signal responsive thereto; and
a control unit, configured to receive the sensor signal, and, responsive thereto, to:
sequentially drive the electrode devices to apply to the nervous tissue respective currents, with delays between driving each of the electrode devices that are timed to the first velocity of the propagation of the body-generated action potentials so as to minimize undesired blocking of the body-generated action potentials propagating through the first type of the nerve fibers,
configure the currents to induce respective first orthodromic electrode-generated action potentials that propagate in the nervous tissue in a first direction, so as to treat the condition, and
configure the currents to suppress respective second electrode-generated action potentials from propagating in the nervous tissue in a second direction opposite the first direction.

46. Apparatus according to claim 45, wherein the control unit is configured to drive the electrode devices to configure the currents to induce the first orthodromic action potentials to propagate in the nervous tissue in an afferent direction with respect to a central nervous system of the subject, so as to treat the condition.

47. Apparatus according to claim 46, wherein the longitudinal tissue includes a vagus nerve of the subject, and wherein the electrode devices are configured to be coupled to the vagus nerve.

48. Apparatus according to claim 45, wherein the control unit is configured to drive the electrode devices to configure the currents to induce the first electrode-generated orthodromic action potentials to propagate in the nervous tissue in an efferent direction with respect to a central nervous system of the subject, so as to treat the condition.

49. Apparatus according to claim 48, wherein the longitudinal tissue includes a vagus nerve of the subject, and wherein the electrode devices are configured to be coupled to the vagus nerve.

50. Apparatus according to claim 45, wherein the control unit is configured to: (a) drive the electrode devices to apply the currents, and (b) suppress the second electrode-generated action potentials, at substantially the same time.

51. Apparatus according to claim 45, wherein the control unit is configured to regulate the suppressing of the second electrode-generated action potentials so as to inhibit an undesired response of a central nervous system of the subject generated responsive to the electrode devices applying the currents to the nervous tissue.

52. Apparatus according to claim 45, wherein the control unit is configured to regulate the suppressing of the second electrode-generated action potentials so as to inhibit an undesired sensation generated responsive to the electrode devices applying the currents to the nervous tissue.

53. Apparatus according to claim 45, wherein the control unit is configured to regulate the suppressing of the second electrode-generated action potentials so as to suppress second electrode-generated action potentials induced responsive to the electrode device applying the currents.

54. Apparatus according to claim 45, wherein the condition is selected from the group consisting of: a gastrointestinal motility disorder of the subject, an eating disorder of the subject, obesity of the subject, anorexia of the subject, a gastrointestinal tract disorder of the subject, hypertension of the subject, and coma of the subject, and wherein the control unit is configured to configure the currents so as to be capable of treating the selected condition.

55. Apparatus according to claim 45, wherein the condition is selected from the group consisting of: Parkinson's disease, and tremor, and wherein the control unit is configured to configure the currents so as to be capable of treating the selected condition.

56. Apparatus according to claim 45, wherein the longitudinal tissue includes a vagus nerve of the subject, wherein the electrode devices are configured to be coupled to the vagus nerve, and wherein the control unit is configured to: (a) configure the currents so as to be capable of treating epilepsy of the subject, and (b) suppress second electrode-generated action potentials that interfere with an ability of the subject to speak.

57. Apparatus according to claim 45, wherein the longitudinal tissue includes a vagus nerve of the subject, wherein the electrode devices are configured to be coupled to the vagus nerve, and wherein the control unit is configured to configure the currents so as to be capable of inducing constriction of a lower esophageal sphincter of the subject.

58. Apparatus according to claim 45, wherein the longitudinal tissue is selected from the group consisting of: longitudinal nervous tissue of a central nervous system of the subject, and longitudinal nervous tissue of a peripheral nervous system of the subject, and wherein the electrode devices are configured to be coupled to the selected tissue.

59. Apparatus according to claim 45, wherein the control unit is configured to regulate the suppressing of the second electrode-generated action potentials from propagating in the second direction so as to inhibit an undesired effector action responsive to driving the electrode devices to apply the currents to the nervous tissue.

60. Apparatus according to claim 45, wherein the sensor is configured to sense the indication by sensing at least one physiological parameter of the subject selected from the group consisting of: electroencephalographic (EEG) waves, respiration changes, heart rate changes, an aura, and a motor effect.

61. Apparatus according to claim 45, wherein the condition includes a gastrointestinal motility disorder of the subject, and wherein the sensor is configured to sense the indication by sensing at least one physiological parameter of the subject selected from the group consisting of: a pattern of contractions of a portion of a gastrointestinal tract of the subject, and digestion by the subject.

62. Apparatus according to claim 45, wherein the condition includes a sleep disorder of the subject, and wherein the sensor is configured to sense the indication by sensing at least one physiological parameter of the subject selected from the group consisting of: a respiration pattern of the subject indicative of wakefulness during normal nocturnal hours, abdominal impedance changes associated with respiration by the subject indicative of the sleep disorder, a sustained abnormal period of cessation of respiration of the subject, respiration typically associated with a state of sleeplessness of the subject, electroencephalographic (EEG) activity of the subject, a sudden uncontrolled nodding of the head of the subject, abdominal impedance of the subject, and eye movement of the subject.

63. Apparatus according to claim 45, wherein the indication includes swallowing by the subject, and wherein the sensor comprises one or more electrodes configured to be implanted in a vicinity of an esophagus of the subject, and to detect the swallowing.

64. Apparatus according to claim 45, wherein the condition includes an eating disorder of the subject, and wherein the indication includes a quantity of food consumed by the subject in a predetermined period of time, and wherein the sensor is configured to sense the quantity.

65. Apparatus according to claim 45, wherein the condition includes an eating disorder of the subject, and wherein the indication includes an amount of food in a stomach of the subject, and wherein the sensor comprises one or more electrodes configured to be secured to an outer wall of the stomach, and to sense the amount of the food in the stomach.

66. Apparatus according to claim 45, wherein the sensor is configured to sense the indication by sensing blood pressure of the subject.

67. Apparatus according to claim 45, wherein the control unit is configured to drive the electrode devices to apply respective electric fields to the nervous tissue configured to suppress the second electrode-generated action potentials.

68. A method for treating a condition of a subject, comprising:
identifying that the subject suffers from the condition; and treating the condition by:
sequentially driving currents into respective longitudinal sites of a vagus nerve of the subject having a first set of fibers and a second set of fibers, through which first body-generated action potential propagate at a first velocity, and second body-generated action potentials propagate at a second velocity, respectively, the first set of fibers having diameters generally different from diameters of the second set of fibers, with delays between driving each of the currents that are timed to the first velocity so as to minimize undesired blocking of the first body-generated action potentials propagating through the first set of fibers;
configuring the currents to induce respective first orthodromic electrode-generated action potentials that propagate in the vagus nerve in a first direction, so as to treat the condition, and to suppress respective second electrode-generated action potentials from propagating in the vagus nerve in a second direction opposite to the first direction.

69. A method according to claim 68, wherein configuring the currents comprises configuring the currents to induce the first orthodromic electrode-generated action potentials to propagate in an afferent direction with respect to a central nervous system of the subject.

70. A method according to claim 68, wherein configuring the currents comprises configuring the currents to induce the first orthodromic electrode-generated action potentials to propagate in an efferent direction with respect to a central nervous system of the subject.

71. A method according to claim 68, wherein the condition is selected from the group consisting of: a gastrointestinal motility disorder of the subject, an eating disorder of the subject, obesity of the subject, anorexia of the subject, a gastrointestinal tract disorder of the subject, hypertension of the subject, and coma of the subject, and wherein identifying comprises identifying that the subject suffers from the selected condition.

72. A method according to claim 68, wherein suppressing the second action potentials comprises suppressing the second action potentials repeatedly, during a series of temporally non-contiguous action potential suppression periods, and wherein the method comprises substantially withholding the suppressing of the second action potentials between the action potential suppression periods.

73. A method according to claim 68, and comprising sensing an indication of a presence of the condition, wherein driving the currents comprises driving the currents responsive to sensing the indication.

74. A method according to claim 68, wherein the condition is selected from the group consisting of:

migraine headache, depression, and stroke, and wherein identifying comprises identifying that the subject suffers from the selected condition.

* * * * *